US010768665B2

(12) United States Patent
Aimone et al.

(10) Patent No.: US 10,768,665 B2
(45) Date of Patent: *Sep. 8, 2020

(54) SYSTEM AND METHOD FOR ENHANCED TRAINING USING A VIRTUAL REALITY ENVIRONMENT AND BIO-SIGNAL DATA

(71) Applicant: INTERAXON INC., Toronto (CA)

(72) Inventors: Christopher Allen Aimone, Toronto (CA); Trevor C E Coleman, Toronto (CA); Ariel Stephanie Garten, Toronto (CA); Kapil Jay Mishra Vidyarthi, Toronto (CA); Locillo (Lou) Giuseppe Pino, Cambridge (CA); Michael Apollo Chabior, Oakville (CA); Paul Harrison Baranowski, Toronto (CA); Raul Rajiv Rupsingh, Brampton (CA); Madeline Ashby, Toronto (CA); Paul V Tadich, Toronto (CA)

(73) Assignee: INTERAXON INC., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/144,854

(22) Filed: Sep. 27, 2018

(65) Prior Publication Data

US 2019/0033914 A1 Jan. 31, 2019

Related U.S. Application Data

(63) Continuation of application No. 14/851,853, filed on Sep. 11, 2015, now Pat. No. 10,120,413.
(Continued)

(51) Int. Cl.
*G06F 1/16* (2006.01)
*G06F 3/01* (2006.01)
(Continued)

(52) U.S. Cl.
CPC .............. *G06F 1/163* (2013.01); *A61B 3/113* (2013.01); *A61B 5/0006* (2013.01);
(Continued)

(58) Field of Classification Search
CPC .......... G06F 3/012; G06F 3/011; G06F 1/163; G06F 3/015; G06F 3/016; G06F 2203/011
See application file for complete search history.

(56) References Cited

U.S. PATENT DOCUMENTS 5,649,061 A 7/1997 Smyth
6,012,926 A * 1/2000 Hodges ................. A61M 21/00
434/236

(Continued)

OTHER PUBLICATIONS

USPTO, Office Action for U.S. Appl. No. 14/851,853 dated Mar. 31, 2017.
(Continued)

*Primary Examiner* — Towfiq Elahi
(74) *Attorney, Agent, or Firm* — Norton Rose Fulbright Canada LLP

(57) ABSTRACT

A training apparatus has an input device and a wearable computing device with a bio-signal sensor and a display to provide an interactive virtual reality ("VR") environment for a user. The bio-signal sensor receives bio-signal data from the user. The user interacts with content that is presented in the VR environment. The user interactions and bio-signal data are scored with a user state score and a performance scored. Feedback is given to the user based on the scores in furtherance of training. The feedback may update the VR environment and may trigger additional VR events to continue training.

20 Claims, 16 Drawing Sheets

Related U.S. Application Data

(60) Provisional application No. 62/048,923, filed on Sep. 11, 2014.

(51) Int. Cl.

| | |
|---|---|
| *A61B 3/113* | (2006.01) |
| *A61B 5/16* | (2006.01) |
| *A61B 5/00* | (2006.01) |
| *A61B 5/11* | (2006.01) |
| *A61B 5/0476* | (2006.01) |
| *A61B 5/0484* | (2006.01) |
| *G16H 40/67* | (2018.01) |
| *G06F 19/00* | (2018.01) |
| *A61B 5/0402* | (2006.01) |

(52) U.S. Cl.
CPC .......... *A61B 5/0022* (2013.01); *A61B 5/0024* (2013.01); *A61B 5/0476* (2013.01); *A61B 5/04842* (2013.01); *A61B 5/04845* (2013.01); *A61B 5/1114* (2013.01); *A61B 5/16* (2013.01); *A61B 5/165* (2013.01); *A61B 5/486* (2013.01); *A61B 5/6803* (2013.01); *A61B 5/6814* (2013.01); *A61B 5/6821* (2013.01); *A61B 5/6831* (2013.01); *A61B 5/7203* (2013.01); *A61B 5/7264* (2013.01); *A61B 5/744* (2013.01); *A61B 5/7445* (2013.01); *G06F 3/011* (2013.01); *G06F 3/012* (2013.01); *G06F 3/015* (2013.01); *G06F 3/016* (2013.01); *G06F 19/00* (2013.01); *G16H 40/67* (2018.01); *A61B 5/0402* (2013.01); *A61B 2503/12* (2013.01); *A61B 2560/0475* (2013.01); *A61B 2560/0493* (2013.01); *A61B 2562/0219* (2013.01); *A61B 2562/125* (2013.01); *A61B 2562/164* (2013.01); *A61B 2562/166* (2013.01); *G06F 2203/011* (2013.01)

(56) References Cited

U.S. PATENT DOCUMENTS

| | | | |
|---|---|---|---|
| 6,186,145 B1* | 2/2001 | Brown | A63F 13/005 |
| | | | 128/897 |
| 6,425,764 B1 | 7/2002 | Lamson | |
| 8,149,241 B2 | 4/2012 | Do et al. | |
| 8,392,250 B2 | 3/2013 | Pradeep et al. | |
| 8,396,744 B2 | 3/2013 | Pradeep et al. | |
| 2002/0128540 A1 | 9/2002 | Kim et al. | |
| 2002/0128541 A1 | 9/2002 | Kim et al. | |
| 2008/0275358 A1* | 11/2008 | Freer | G09B 7/02 |
| | | | 600/544 |
| 2009/0137922 A1 | 5/2009 | Soderlund | |
| 2011/0040155 A1 | 2/2011 | Guzak et al. | |
| 2013/0089851 A1 | 4/2013 | Drane et al. | |
| 2015/0382071 A1 | 12/2015 | Aravamudan | |

OTHER PUBLICATIONS

USPTO, Office Action for U.S. Appl. No. 14/851,853 dated Jul. 21, 2017.

USPTO, Office Action for U.S. Appl. No. 14/851,853 dated Nov. 6, 2017.

Clay B. Holroyd et al., Reward prediction error signals associated with a modified time estimation task, Psychophysiology, 44 (2007), 913-917.

Kyle E. Mathewson et al., Different slopes for different folks: Alpha and delta EEG power predict subsequent video game learning rate and improvements in cognitive control tasks, Psychophysiology, 49 (2012), 1558-1570.

Linda Elder, Critical Thinking and Emotional Intelligence, Inquiry: Critical Thinking Across the Disciplines, Winter, 1996, vol. XVI, No. 2.

* cited by examiner

TABLE 5A - EXAMPLE DETERMINE FEEDBACK 453

| USER STATE SCORE 435 | PERFORMANCE SCORE 440 | EXAMPLE FEEDBACK 453 |
|---|---|---|
| LOW | LOW | CONSIDER FAILING STUDENT OR REQUIRING THEM TO COMPLETE ADDITIONAL PREREQUISITE COURSES |
| LOW | HIGH | GIVE FEEDBACK TO USER TO HELP IMPROVE USER STATE. REVISE THEIR TRAINING 480 TO TEACH USER 305 MEDITATION TO HANDLE ANXIETY |
| HIGH | LOW | REPEAT SAME VR EVENT 430 OVER AND OVER AGAIN TO IMPROVE TECHNICAL SKILL |
| HIGH | HIGH | PASSING GRADE - STUDENT HAS COMPLETED REQUIREMENTS OF THIS TRAINING PROGRAM |

TABLE 5B - EXAMPLE OF SCORING SYSTEM IN DRIVER TRAINING

| VR EVENT | EXPECTED PERFORMANCE | ACTUAL PERFORMANCE | PERFORMANCE SCORE | EXPECTED USER STATE | ACTUAL USER STATE | USER STATE SCORE |
|---|---|---|---|---|---|---|
| SLIGHT SWERVE OF TRUCK IN RIGHT LANE AHEAD | REDUCE SPEED AND INCREASE DISTANCE BETWEEN CAR AND TRUCK | MAINTAINS SAME SPEED | MEDIUM | INCREASED ATTENTION; OCCASIONAL EYE GAZE TOWARDS TRUCK | VERY LITTLE CHANGE INATTENTION OR EYE GAZE | LOW |
| LARGE SWERVE OF TRUCK IN RIGHT LANE ADJACENT TO CAR | SWERVE ONTO SHOULDER; HONK HORN TO WARN TRUCK DRIVER; REDUCE SPEED BY SLIGHT BRAKING | HONK HORN REPEATEDLY | LOW | INCREASE VIGILANCE; CALM STATE OF MIND | EXTREME ANXIETY | POOR |

FIG. 5

SYSTEM AND METHOD FOR ENHANCED TRAINING USING A VIRTUAL REALITY ENVIRONMENT AND BIO-SIGNAL DATA

CROSS-REFERENCE TO RELATED APPLICATION(S)

This application is a continuation of U.S. patent application Ser. No. 14/851,853, filed on Sep. 11, 2015, and claims all benefit, including priority, of U.S. Provisional Patent Application Ser. No. 62/048,923, filed Sep. 11, 2014 and entitled SYSTEM AND METHOD FOR DETERMINING MENTAL RESPONSE TO A VIRTUAL ENVIRONMENT, the contents of which are incorporated herein by reference, in their entirety.

FIELD

Embodiments described herein relate to wearable devices. Embodiments described herein relate more particularly to wearable devices with bio-signal sensors for training.

BACKGROUND

A computing device may include a display to provide visual output data for the user. A virtual reality (VR) environment may be displayed on the display to provide a computer simulation of real world elements. A user may provide input to a computing device for example using a keyboard, mouse, track pad, touch screen, or motion-capture devices.

A human brain generates bio-signals such as electrical patterns known, which may be measured/monitored using an electroencephalogram ("EEG"). These electrical patterns, or brainwaves, are measurable by devices such as an EEG. Typically, an EEG will measure brainwaves in an analog form. Then, these brainwaves may be analyzed either in their original analog form or in a digital form after an analog to digital conversion.

BRIEF DESCRIPTION OF THE DRAWINGS

Embodiments will now be described, by way of example only, with reference to the attached figures, wherein:

FIG. 5 a schematic of an implementation of determine feedback operation using Tables 5A and 5B according to some embodiments;

Figure 1:
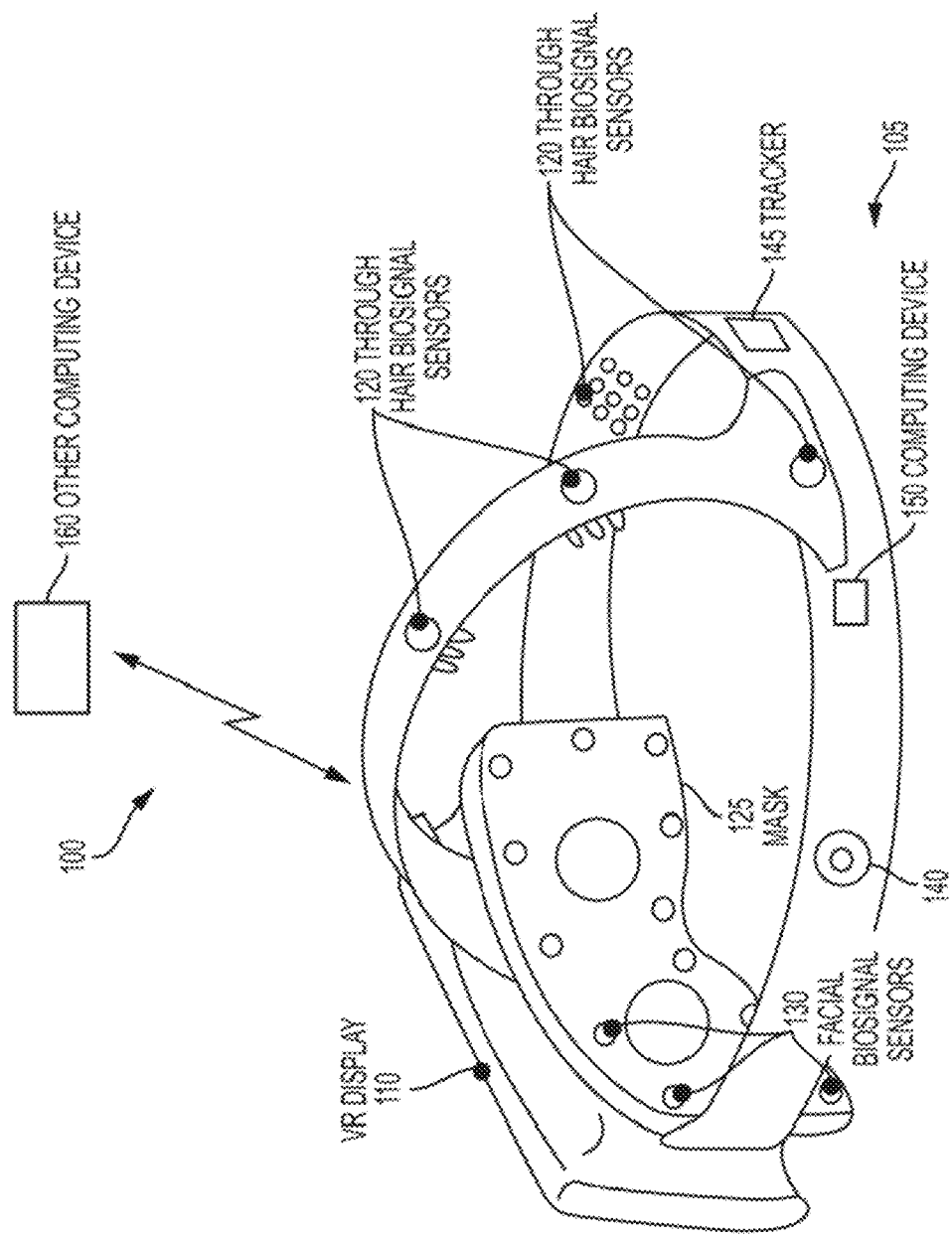
FIG. 1 is a perspective view of an implementation of an example device to provide a VR environment according to some embodiments.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION

Reference will now be made in detail to some specific examples embodiments including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. Also, it is to be understood that the phraseology and terminology employed herein are for the purpose of illustrative description and should not be regarded as limiting.

For example, the techniques and mechanisms of various embodiments are described in the context of particular tasks or functions in the training of humans. As the ways in which humans interact with computing devices change, computers may become usable for new purposes or may be specifically configured to be more efficient in performing existing tasks. Embodiments described herein may involve measuring and analyzing bio-signals such as brainwave patterns for a variety of practical applications including improving the training of humans for performing certain tasks or functions. It should be noted that the techniques and mechanisms of the embodiments described herein apply to a variety of different tasks or functions in the training of humans.

Embodiments described herein may provide an integrated computing device or system with an interactive VR environment with visual output data to provide a computer simulation of physical elements for training. A user may interact with the VR environment using various input devices including bio-signal sensors and in response the VR environment may update or modify to provide enhanced training applications.

In the following description, numerous specific details are set forth in order to provide a thorough understanding of the present invention. Particular example embodiments may be implemented without some or all of these specific details. In other instances, well known process operations have not been described in detail in order not to unnecessarily obscure the present invention.

Various techniques and mechanisms of the embodiments described herein will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors. As an illustrative example, a wearable device may include a processor that may in turn connect to a client device with another processor. The wearable device, client device, or both, may also connect to a cloud server system with a processor. Furthermore, the techniques and mechanisms of the embodiments described herein will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory, Consequently, a connection does not necessarily mean a direct, unimpeded connection unless otherwise noted.

According to an aspect of embodiments described herein, there is provided training apparatus with an input device and a wearable computing device with a bio-signal sensor and a display to provide an interactive VR environment for a user, the bio-signal sensor receives bio-signal data from the user, the bio-signal sensor comprising a brainwave sensor. VR may provide a computer simulated experience that replicates, creates or enhances an environment that simulates physical presence in places in the real or non-real world. A VR environment may also refer to an augmented reality environment which may be a live direct or indirect view of a physical, real-world environment whose elements are augmented or supplemented by computer processes. A user may interact in that world using input data such as gesture data, manual input, sensor data, and so on. The computing device having or in communication with a processor configured to as part of the interactive VR environment, present content on the display where the content has a VR event, desired user states, and desired effects; receive user manual inputs from the input device which have effects in the interactive VR environment including during the VR event. In response, the processor receives the bio-signal data of the user from the bio-signal sensor during the VR event and processes the bio-signal data to determine user states of the user, including brain states, during the VR event, where the user states are processed using a user profile stored in a data storage device accessible by the processor and the user states include brain states. The processor determines a user state score by comparing the user states of the user to the desired user states during the course of the VR event and determines a performance score by comparing the effects to the desired effects during the course of the VR event. The processor provides feedback to the user where the feedback is based on a combination of the user state score and the performance score.

In some embodiments, the feedback may be provided as a visual representation in the VR environment to have effects in the VR environment, including during the VR event to provide visual, real time or near real time feedback. The feedback may be an additional VR event (as part of a sequence of VR events or otherwise) to restart the bio-signal acquisition and scoring operations and to provide additional feedback to the user.

In some embodiments, there may be multiple VR events provided as a sequence of VR events as part of a training program. The sequence may be a dynamic sequence that may modify or vary based on the user state score or other aspects of the VR environment or user states.

In some embodiments, the wearable computing device has an inertial sensor and the bio-signal sensor further comprises a facial bio-signal sensor, and where the bio-signal data further comprises data from the facial bio-signal sensor and the inertial sensor; the computing device is further configured to receive the bio-signal data from the facial bio-signal sensor and the inertial sensor for a user head and eye gaze direction, wherein the user states further comprises the user head and eye gaze direction, and the desired user states further comprises a desired user head and eye gaze direction.

In some embodiments, the brain states has one or more of ability of operator to learn; prediction error; and emotional state leading to impaired thinking.

In some embodiments, the device presents the user state score and the performance score synchronized with the content and the VR event to assist the user to better attain the desired user states and desired manual inputs on the input device.

In some embodiments, the computing device is further configured to: revise the content in response to the feedback provided to the user where the user is further trained on the revised content. In some embodiments, the revised content has further effects in the interactive VR environment including during the VR event to update or modify the VR environment. In some embodiments, the revised content is a revised VR event, revised desired user states, and/or revised desired effects to provide an iterative and cyclical training process.

In some embodiments, the user state score further comprises failure brain states.

In some embodiments, the display is a stereoscopic display.

In some embodiments, the apparatus has a second display for presenting the content and a visual representation of the user states and manual inputs of the user in real time.

In some embodiments, the computing device having or in communication with the processor is further configured to: provide real time or near real time feedback to the user during the presentation of the content. The real time or near real time feedback may occur during the VR event.

In some embodiments, the VR event is associated with event time data and a portion of bio-signal data is associated with bio-signal time data corresponding to the event time data, wherein the processor is configured to identify a portion of the bio-signal data based on the event time data and process the portion of the bio-signal data to determine the user states during the VR event, the bio-signal time data synchronized to the event time data using a common timeline or clock or a synchronization or context operation.

In some embodiments, the VR event is associated with event time data and the bio-signal data is associated with bio-signal time data, and wherein the processor is configured to identify a time interval based on an expected response time for the VR event and the event time data, identify a portion of the bio-signal data based on the time interval and the bio-signal time data, and process the portion of the bio-signal data to determine the user states during the VR event, the bio-signal time data synchronized to the event time data.

According to an aspect of embodiments described herein, there is provided training apparatus with an input device, a display and a wearable computing device with a bio-signal sensor to provide an interactive virtual reality ("VR") environment for a user. The bio-signal sensor receives bio-signal data from the user, the bio-signal sensor comprising a brainwave sensor.

In some embodiments, the computing device having or in communication with a processor configured to as part of the interactive VR environment, present content on the display where the content has a training program as a sequence of VR events, desired user states, and desired effects; receive user manual inputs from the input device which have effects in the interactive VR environment including during one or more VR events of the training program. In response, the processor receives the bio-signal data of the user from the bio-signal sensor during the VR event of the training program and processes the bio-signal data to determine user states of the user, including brain states, during the VR event of the training program, where the user states are processed using a user profile stored in a data storage device accessible by the processor and the user states include brain states. The processor determines a user state score by comparing the user states of the user to the desired user states during the course of the training program and determines a performance score by comparing the effects to the desired effects during the course of the training program. The processor provides feedback to the user where the feedback is based on a combination of the user state score and the performance score. The feedback may be provided as a visual representation in the VR environment to have effects in the VR environment, including during the VR event to provide visual, real time or near real time feedback. The feedback may be an additional VR event (as part of a sequence of VR events or otherwise) to restart the bio-signal acquisition and scoring operations and to provide additional feedback to the user.

According to an aspect of embodiments described herein, there is provided training apparatus with an input device and a wearable computing device with a bio-signal sensor, the wearable device in connection with a display to provide an interactive virtual reality ("VR") environment for a user. The bio-signal sensor receives bio-signal data from the user, the bio-signal sensor comprising a brainwave sensor. The computing device having or in communication with a processor configured to as part of the interactive VR environment, present content on the display where the content has a VR event, desired user states, and desired effects; receive user manual inputs from the input device which have effects in the interactive VR environment including during the VR event. In response, the processor receives the bio-signal data of the user from the bio-signal sensor during the VR event and processes the bio-signal data to determine user states of the user, including brain states, during the VR event where the VR event is linked to the bio-signal data based on timing data, where the user states are processed using a user profile stored in a data storage device accessible by the processor and the user states include brain states. The processor determines a user state score by comparing the user states of the user to the desired user states during the course of the VR event and determines a performance score by comparing the effects to the desired effects during the course of the VR event. The processor provides feedback to the user where the feedback is based on a combination of the user state score and the performance score. The feedback may be provided as a visual representation in the VR environment to have effects in the VR environment, including during the VR event to provide visual, real time or near real time feedback. The feedback may be an additional VR event (as part of a sequence of VR events or otherwise) to restart the bio-signal acquisition and scoring operations and to provide additional feedback to the user.

In another aspect, there is provided a training method implemented using an input device and a wearable computing device having or in communication with a processor, a bio-signal sensor and a display to provide an interactive virtual reality ("VR") environment for a user, the bio-signal sensor receives bio-signal data from the user, the bio-signal sensor comprising a brainwave sensor; the training method involving: as part of the interactive VR environment, presenting content on the display where the content has a VR event, desired user states, and desired effects; receiving user manual inputs from the input device which have effects in the interactive VR environment including during the VR event; receiving the bio-signal data of the user from the bio-signal sensor during the VR event; processing the bio-signal data to determine user states of the user, including brain states, during the VR event, the user states are processed using a user profile stored in a data storage device accessible by the processor and the user states include brain states; determining a user state score by comparing the user states of the user to the desired user states during the course of the VR event; determining a performance score by comparing the effects to the desired effects during the course of the VR event; and providing feedback to the user wherein the feedback is based on a combination of the user state score and the performance score.

In some embodiments, the wearable computing device further comprises an inertial sensor and the bio-signal sensor further comprises a facial bio-signal sensor, and where the bio-signal data further comprises data from the facial bio-signal sensor and the inertial sensor; the method further comprising receiving the bio-signal data from the facial bio-signal sensor and the inertial sensor for a user head and eye gaze direction; wherein the user states further comprises the user head and eye gaze direction, and the desired user states further comprises a desired user head and eye gaze direction.

In some embodiments, the brain states comprises one or more of ability of operator to learn; prediction error; and emotional state leading to impaired thinking.

In some embodiments, the method further involves post presenting the user state score and the performance score synchronized with the content and the VR event to assist the user to better attain the desired user states and desired manual inputs on the input device.

In some embodiments, the method further involves revising the content in response to the feedback provided to the user where the user is further trained on the revised content.

In some embodiments, the user state score further comprises failure brain states.

In some embodiments, the display is a stereoscopic display.

In some embodiments, the method further involves presenting the content and the user states and manual inputs of the user in real time on a second display.

In some embodiments, the method further involves providing real time feedback to the user during the presentation of the content.

Referring to FIG. 1 in accordance with an exemplary implementation of embodiments described herein, there is provided a perspective view of a training system 100 with a wearable device 105 and other computing device 160. The wearable device 105 has a stereoscopic display 110; bio-signal sensors 120; facial bio-signal sensors 130; sound generator 140; a computing device 150; tracker 145; and user manual inputs such as mouse, joystick, or keyboard (not shown). The other computing device 160 and the computing device 150 may be, for example, a computer, embedded computer, server, laptop, tablet, or mobile phone. The stereoscopic display 110 is a 3-dimensional (3D) (or dual 2-dimensional (2D) images giving "3D") display, but alternatively may be a 2-dimensional (2D) display.

The other computing device 160 is in communication with the wearable device 105 and provides the wearable device 105 with content to create a VR (Virtual Reality) environment. The VR environment includes an interactive VR environment where content presented on the display may update or modify in response to input from bio-signal sensors 130, other sensors, user manual inputs, or other inputs, for example. The other computing device 160 may also be a server over the Internet or other network. In other embodiments, the functions of the other computing device 160 are incorporated into the computing device 150. In further embodiments, the functions of the computing device 150 are incorporated into the other computing device 160.

The tracker 145 is an inertial sensor for measuring movement of the wearable device 105. It detects the 3-dimensional coordinates of the wearable device 105 and accordingly its user's location, orientation or movement in the VR environment including the user's gaze direction. The tracker 145, for example, comprises one or more accelerometers and/or gyroscopes. The sound generator 140, for example, comprises one or more speakers, microphones, and/or head phones.

In various implementations, the wearable device 105 may include a variety of other sensors, input devices, and output devices. For example, the wearable device 105 may comprise touch sensor for receiving touch input from the user and tactile device for providing vibrational and force feedback to the user. The training system 100 may further include input devices such as mouse, keyboard and joystick.

The wearable device 105 is, for example, a wearable headset worn on a user's head. The computing device 150 of the wearable device 105 is configured to create a VR environment on the stereoscopic display 110 and sound generator 140 for presentation to a user; receive bio-signal data of the user from the bio-signal sensors 120, at least one of the bio-signal sensors 120 comprising a brainwave sensor, and the received bio-signal data comprising at least brainwave data of the user; and determine brain state response elicited by the VR environment at least partly by determining a correspondence between the brainwave data and a predefined bio-signal measurement stored in a user profile, the predefined bio-signal measurement associated with predefined brain state response type. The brain state response may comprise an emotional response type. The wearable device 105 may be called a virtual reality headset.

The VR (stereoscopic) display 110 is positioned for viewing through an eye mask 125 wearable by a user. The eye mask 125 comprises an aperture for each eye, and a plurality of facial bio-signal sensors 130 positioned on the mask for contacting the user's face when the wearable device 105 is worn. One or more straps, which may optionally be adjustable, are attached to the eye mask 125 or display portion of the wearable device 105. Optionally, bio-signal sensors may be positioned along one or more of the straps to sense brainwave activity in the user through the user's head. Sensors positioned along the straps may be specifically configured to travel a distance from the strap, past the user's hair, if any, to the user's scalp. Accordingly, any such sensors may include an elongated contact area, which is optionally of a resilient construction. The facial bio-signal sensors 130 measure, include, electrical bio-signals such as EEG, EMG (Electromyograph) and EOG (Electrooculography), as well as FNIRS (functional near infrared spectroscopy). The materials used to support the device on the face may be opaque to the wavelengths used by the FNIRS sensors such that ambient light can be reduced and thus increase the signal to noise ratio for the sensor.

Electrical signals may be measured on other regions of the head and may be mounted to the supporting architecture of the display device. Typically these are elasticized fabric. Sensors that measure scalp potentials would typically have a fingered design to allow the conductive electrodes to reach through the hair to reach the surface of the scalp. The fingers should be springy to allow for comfort and allow for the user to manipulate them in a fashion that will spread and disperse hair to facilitate a low impedance interface to skin of the scalp. Capacitive electrodes may also be used. These would allow for a slight air between the electrode and the scalp. Many electrodes should be used if possible to allow for a higher dimensional bio-signal to facilitate denoising signal processing and to acquire more accurate spatial information of the bio-signal activity. Good spatial resolution will allow more precise interpretation of the electrical activity in the brain as well as muscular activity in the face and head—which are vital for accurate emotion estimation. Facial bio-signal sensors 130 further yield facial expression information (which is difficult to obtain using cameras in a VR headset.). Muscles specifically around the eyes play an important role in conveying emotional state. Smiles for example if accompanied by engagement of the muscles at the corners of the eyes are interpreted as true smiles, as opposed to those that are put on voluntarily. EOG signals give information about eye movements. Basic gaze direction and dynamic movement can be estimated in real-time and can thus be used as a substitute for optical methods of eye tracking in many applications. Measurement of the EOG signal is also important for noise free interpretation of the EEG signal. FNIRS sensors if used can provide supplemental information about activity in the frontal region of the brain with high spatial accuracy. Other sensors tracking other types of eye movement may also be employed.

Embodiments of the training system 100 may provide for the collection, analysis, and association of particular bio-signal and non-bio-signal data with specific brain states for both individual users and user groups. The collected data, analyzed data or functionality of the systems and methods may be shared with others, such as third party applications and other users. Connections between any of the computing devices, internal sensors (contained within the wearable device), external sensors (contained outside the wearable device), user effectors, and any servers may be encrypted. Collected and analyzed data may be used to build a user profile that is specific to a user. The user profile data may be analyzed, such as by machine learning algorithms, either individually or in the aggregate to function as a brain computer interface (BCI), or to improve the algorithms used in the analysis. Optionally, the data, analyzed results, and functionality associated with the system can be shared with third party applications and other organizations through an API. One or more user effectors may also be provided at the wearable device or other local computing device for providing feedback to the user, for example, to vibrate or provide some audio or visual indication to assist the user in achieving a particular mental state, such as a meditative state.

In another aspect of embodiments described herein, the wearable device 105 may be in a form of one or more sensors adapted to being placed at or adhered to the user's head or face. Each sensor may optionally communicate with one another either through wires or wirelessly. Each sensor may optionally communicate with the other computing device 160 either through wires or wirelessly. The other computing device 160 may be mounted to the wearable device 105 in order to reside at or near the user's head or face. Alternatively, the other computing device 160 may be located elsewhere on the user's body, such as in a bag or pocket of the user's clothing or on a band or strap attachable to the user's body. The other computing device 160 may also be disposed somewhere outside the user's body. For example, the sensors may monitor the user, storing data in local storage mounted to the wearable device 105, and once moving into proximity with the other computing device 160, the sensors, or a transmitter of the wearable device 105 may transmit stored data to the other computing device 160 for processing. In this implementation, the wearable device 105 may be predominantly usable by the user when located nearby the other computing device 160.

Optionally, the wearable device 105 may be used to implement aspects of the systems and methods described in PCT Patent Application No. PCT/CA2014/000256, filed Mar. 17, 2014 the entirety of which is incorporated by reference herein. Accordingly, the wearable device 105 may implement a method that may involve acquiring bio-signal measurement from a user using the bio-signal measuring sensor during a VR event. The bio-signal measurement may include brainwave state measurement. The wearable device 105 may process the bio-signal measurement, including at least the brainwave state measurement, in accordance with a profile associated with the user. The wearable device may determine a correspondence between the processed bio-signal measurement and predefined device control action, which may also generate effects in the VR environment. In accordance with the correspondence determination, the wearable device may control operation of component of the wearable device or effects in the VR environment. Various types of bio-signals, including brainwaves, may be measured and used to control the device or the VR environment in various ways. The controlling operation of component of the wearable device may comprise sharing the processed brainwave state measurement with computing device over a communications network. Thresholds of brain state may be learned from each user.

Optionally, the wearable device 105 may be used to implement aspects of the systems and methods described in PCT Patent Application No. PCT/CA2014/000004, filed Jan. 6, 2014 the entirety of which is incorporated by reference herein. Accordingly, the wearable device 105 may be used with a computer system or method for guiding one or more users through a brain state guidance exercise or routine, such as a meditation exercise. This guidance may be referred to as training. The system may execute a brain state guidance routine with a brain state guidance objective; present brain state guidance indication at the computing device for presentation to user, in accordance with the executed brain state guidance routine; receive bio-signal data of the user from the bio-signal sensor during a VR event, of the bio-signal sensor comprising brainwave sensor, and the received bio-signal data comprising at least brainwave data of the user; measure performance of the user relative to brain state guidance objective corresponding to the brain state guidance routine at least partly by analyzing the received bio-signal data; and update the presented brain state guidance indication based at least partly on the measured performance. The presented brain state guidance indication may be feedback that provides effects in the VR environment. The system may recognize, score, and reward states of meditation, thereby optionally gamifying the experience for the user to provide further training. The system, using bio-signal data measurements measured by the wearable device 105, and in particular brainwave state measurements, may change the state of what is displayed on the display of the wearable device. For example, in response to a determination that the user has achieved a particular brain state, or maintained a particular brain state for a period of time, the wearable device may update the display to provide an indication of the determination (e.g. indicating to the user what brain state has been achieved, and, optionally for how long) and may further display an indication of a particular reward assigned to the user in response to the determination.

Optionally, the wearable device 105 may be used to implement aspects of the systems and methods described in PCT Patent Application No. PCT/CA2013/001009, filed Dec. 4, 2013, the entirety of which is incorporated by reference herein. Accordingly, the wearable device 105 may be used with a computer system or method for modulating content based on a person's brainwave data, obtained by the sensors of the wearable apparatus 105 during a VR event 430, including modifying presentation of digital content at a computing device or within the VR environment. The content may also be modulated based on a set of rules maintained by or accessible to the computer system to provide effects within the VR environment. The content may also be modulated based on user input, including through receipt of a presentation control command that may be processed by the computer system of the embodiments described to modify presentation of content. The modification may provide effects in the VR environment. Content may also be shared with associated brain state information to provide additional effects in the VR environment.

Optionally, the wearable device 105 may be used to implement aspects of the systems and methods described in PCT Patent Application No. PCT/CA2013/000785, filed Sep. 16, 2013, the entirety of which is incorporated by reference herein. Accordingly, the wearable device 105 may be used with a computer network implemented system for improving the operation of one or more biofeedback computer systems. The system may include an intelligent bio-signal processing system that is operable to: capture bio-signal data and in addition optionally non-bio-signal data during a VR event 430; and analyze the bio-signal data and non-bio-signal data, if any, so as to: extract one or more features related to individual interacting with the biofeedback computer system; classify the individual based on the features by establishing one or more brainwave interaction profiles for the individual for improving the interaction of the individual with the one or more biofeedback computer systems, and initiate the storage of the brain wave interaction (or bio-signal interaction) profiles to a database (for example, in a cloud); and access one or more machine learning components or processes for further improving the interaction of the individual with the one or more biofeedback computer systems by updating automatically the brainwave interaction profiles based on detecting one or more defined interactions between the individual and the one or more of the biofeedback computer systems.

Each person's brainwaves are different, therefore requiring slightly different tunings for each user. Each person's brain may also learn over time, requiring the system platform to change algorithm parameters over time in order to continue to analyze the person's brainwaves. New parameters may be calculated based on collected data, and may form part of a user's dynamic profile (which may be called bio-signal interaction profile or user profile 335). This user profile 335 may be stored in the cloud, allowing each user to maintain a single profile across multiple computing devices. The user profile 335 may provide parameters used by the user state estimator 325 to determine a user states during a VR event which in turn may be used to compute feedback to the user which may have effects in the VR environment. Other features of the same or another non-limiting exemplary implementation may include: improving algorithms through machine learning applied to collected data either on-board the client device or on the server; saving EEG data along with application state to allow a machine learning algorithm to optimize the methods that transform the user's brainwaves into usable control signals; sharing brainwave data with other applications on mobile device through a cloud services web interface; sharing brainwave data with other applications running on client devices or other devices in the trusted network to provide for the user's brainwave data to control or effect other devices; integration of data from other devices and synchronization of events with brainwave data aid in context aware analysis (during the VR event to provide additional context, for example) as well as storage and future analysis; performing time locked stimulation and analysis to support stimulus entrainment event-related potential ("ERP") analysis; and data prioritization that maximizes the amount of useful information obtainable from an incomplete data download (i.e. data is transmitted in order of information salience).

The wearable device 105 may further be in communication with another computing device, such as a laptop, tablet, or mobile phone such that data sensed by the headset through the sensors may be communicated to the other computing device for processing at the computing device, or at one or more computer servers, or as input to the other computing device or to another computing device. The one or more computer servers may include local, remote, cloud based or software as a service platform (SAAS) servers. Embodiments of the system may provide for the collection, analysis, and association of particular bio-signal and non-bio-signal data with specific mental states for both individual users and user groups. The collected data, analyzed data or functionality of the systems and methods may be shared with others, such as third party applications and other users. Connections between any of the computing devices, internal sensors (contained within the wearable device), external sensors (contained outside the wearable device), user effectors (components used to trigger a user response), and any servers may be encrypted. Collected and analyzed data may be used to build a user profile that is specific to a user. The user profile data may be analyzed, such as by machine learning algorithms, either individually or in the aggregate to function as a brain computer interface, or to improve the algorithms used in the analysis. Optionally, the data, analyzed results, and functionality associated with the system can be shared with third party applications and other organizations through an application programming interface (API). One or more user effectors may also be provided at the wearable device or other local computing device for providing feedback to the user, for example, to vibrate or provide some audio or visual indication in the VR environment to assist the user in achieving a particular mental state, such as a meditative state and provide training to the user.

Sensors usable with the wearable device 105 may come in various shapes and be made of various materials. For example, the sensors may be made of a conductive material, including a conductive composite like rubber or conductive metal. The sensors may also be made of metal plated or coated materials such as stainless steel, silver-silver chloride, and other materials. The sensors include one or more bio-signal sensors 120, such as electroencephalogram (EEG) sensors, galvanometer sensors, electrocardiograph sensors, heart rate sensors, eye-tracking sensors, blood pressure sensors, pedometers, gyroscopes, and any other type of sensor. The sensors may be of various types, including: electrical bio-signal sensor in electrical contact with the user's skin; capacitive bio-signal sensor in capacitive contact with the user's skin; blood flow sensor measuring properties of the user's blood flow; and wireless communication sensor placed sub-dermally underneath the user's skin. Other sensor types may be possible.

In addition to or instead of processing bio-signal measurements on the wearable device 105, the wearable device 105 may communicate with one or more computing devices (for example, the other computing device 160) in order to distribute, enhance, or offload the processing of the bio-signal measurements taken or received by the wearable device. In particular, the one or more computing devices may maintain or have access to one or more databases maintaining bio-signal processing data, instructions, algorithms, associations, or any other information which may be used or leveraged in the processing of the bio-signal measurements obtained by the wearable device. The computing devices may include one or more client or server computers in communication with one another over a near-field, local, wireless, wired, or wide-area computer network, such as the Internet, and of the computers may be configured to receive signals from sensors of the wearable device.

The bio-signal sensor(s) 120 may be provided by a separate wearable device, such as the device described in U.S. Patent Application No. 61/924,020 or International Patent Application No. PCT/CA2015/000003, the entirety of each of which is hereby incorporated by reference, whereby the separate wearable device is in communication with the wearable device of the embodiments described herein, the VR device, or may be used to implement aspects of the wearable device and integrated therewith.

Figure 2:
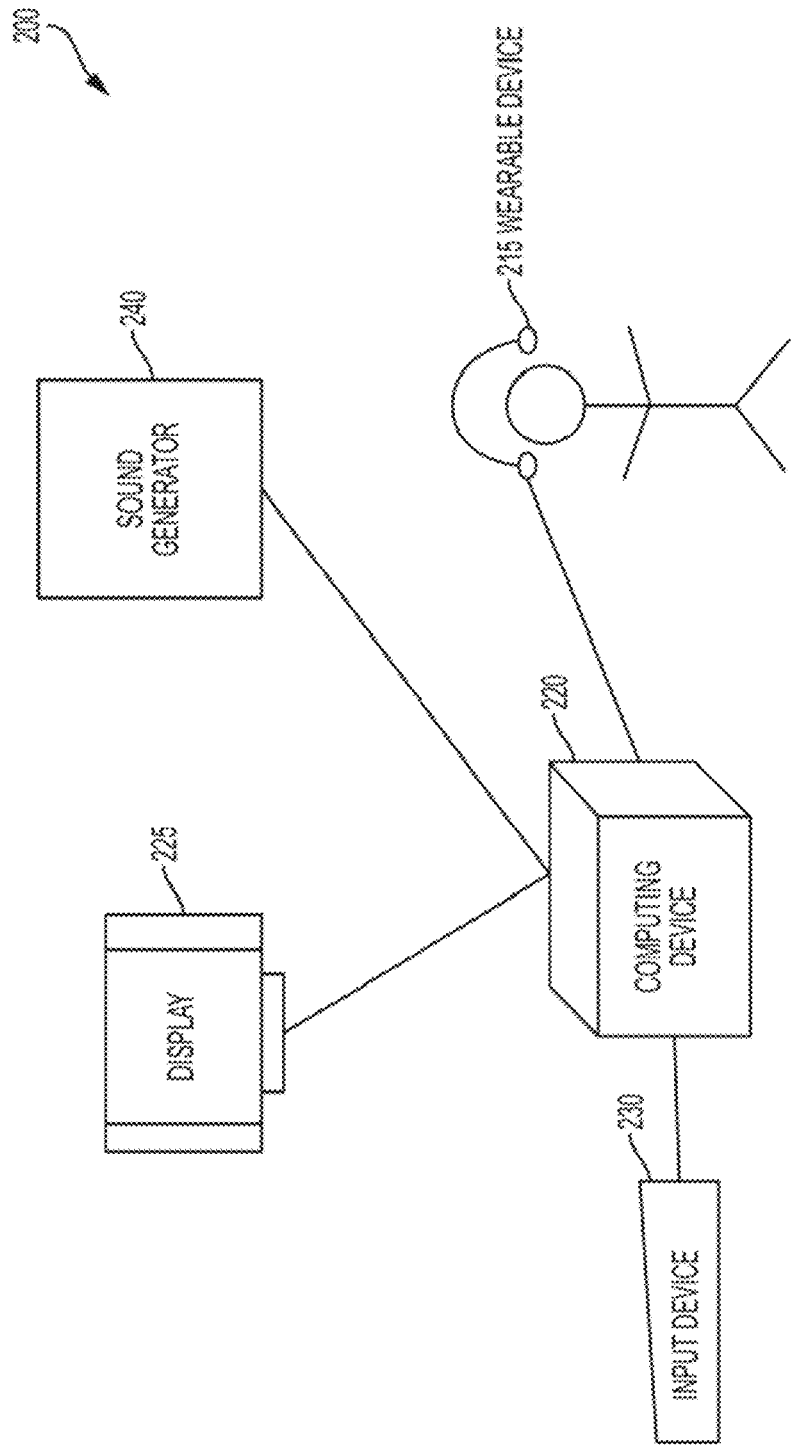
FIG. 2 is a schematic view of an implementation of an example system according to some embodiments.

Referring to FIG. 2 in accordance with another implementation of embodiments described herein, there is provided a perspective view of a training system 200 with a display 225; Input devices 230; sound generator 240; a wearable device 215; and computing device 220. The wearable device 215 has a headset with bio-signal sensors, facial bio-signal sensors and tracker modules with the functionality of corresponding to the bio-signal sensors 120, the facial bio-signal sensors 130, and tracker 145 of FIG. 1. The computing device 220 having the functionality of the other computing device 160 and the computing device 150. The display 225 having the functionality of the stereoscopic display 110. The Input devices 230 and sound generator 240 similarly having the functionality of the input devices and sound generator 140 of FIG. 1.

The other implementation of FIG. 2 may function the same as the exemplary implementation of FIG. 1. An example difference between the implementations is that the display 225 and the sound 240 are not part of the wearable device 215 whereas the display 110 and the sound 140 were part of the wearable device 105. Any disclosure referring to FIG. 1 also apply accordingly to FIG. 2 unless it does not logically apply. The VR environment generated by the other implementation of FIG. 2 may not be as complete as the VR environment generated by the exemplary implementation of FIG. 1, but may provide an adequate interactive VR environment to facilitate training.

Figure 3:
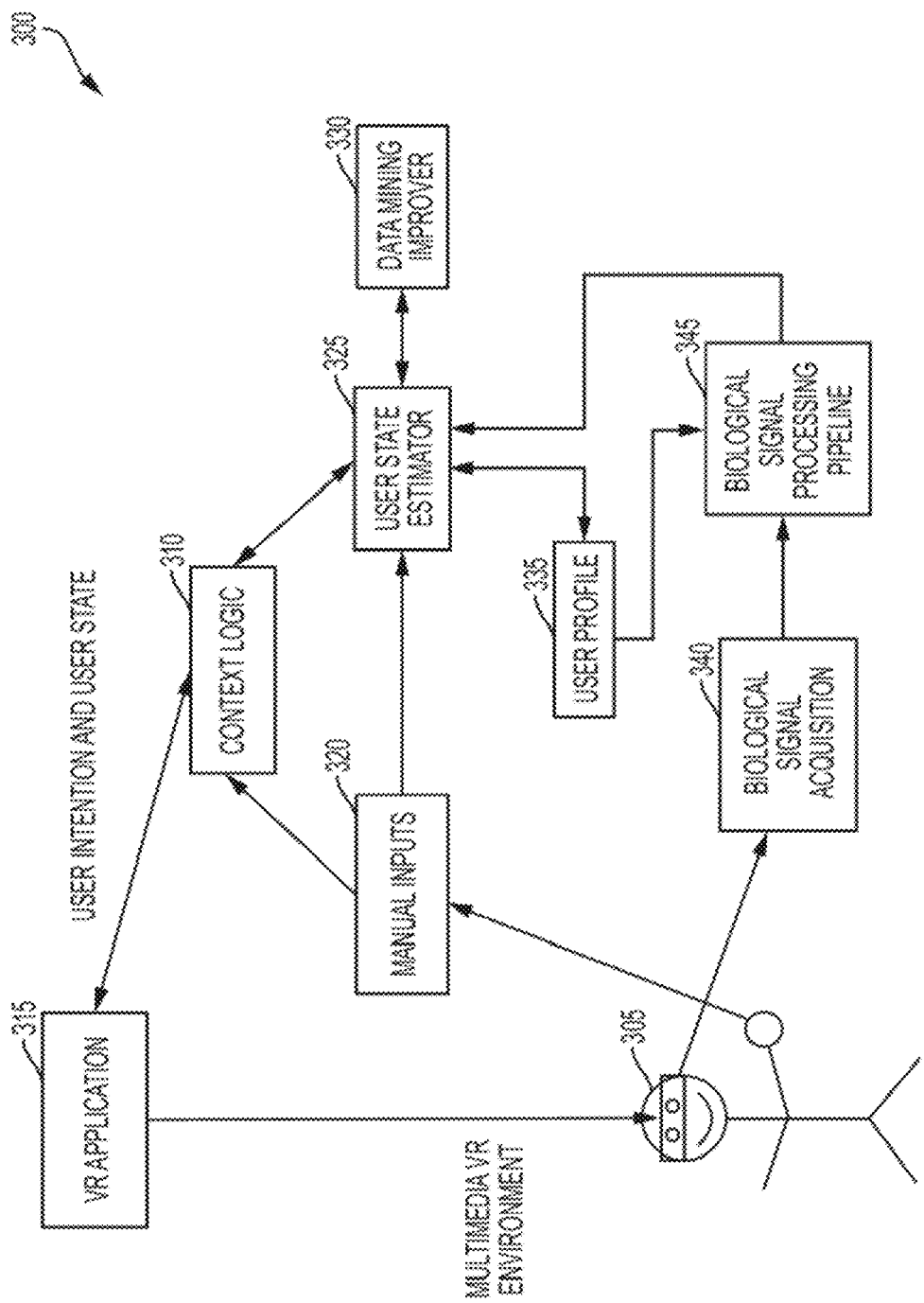
FIG. 3 is a schematic view of an implementation of another example system according to some embodiments.

Referring to FIG. 3 there is shown a system 300 view of an example implementation of the training system 100 of FIG. 1 with a user 305 wearing the wearable device 105. The system 300 may include various hardware and software components such as biological signal acquisition 340; biological signal processing pipeline 345; user state estimator 325; data mining improver 330; context logic 310; manual inputs 320; user profile 335; and VR Application 315.

The user profile 335 contains the signal processing parameters tuned to that user 305 and the parameters for the user's specific prediction models. The signal processing parameters are used by the Biological Signal Processing Pipeline 345 to interpret the user's bio-signal data received during a VR event. The parameters for the prediction models are used by the user state estimator 325 to predict a brain state (e.g. drowsy, or agitated etc.) or other user states such as eye position, high muscle tension etc. during the VR event. The user profile 335 may optionally store the history of all of the user's sessions, raw biological data, processed data, demographic data, etc.

The VR Application 315 uses the user's intention and user state, including brain state, to control the content of a multimedia VR environment presented to the user to provide an interactive environment. The VR Application 315 drives the display 110, sound 140, tactile feedback, etc. to provide effects in the VR environment.

The Biological Signal Acquisition 340 acquires the bio-signal data, including brain state signals, from the bio-signal sensors 120 and 130, and such other sensors that attach to the user's body. The bio-signal data, analog signals, are amplified with high signal to noise ratio.

The Biological Signal Processing Pipeline 345 includes three categories of components: signal processing, feature extraction, and feature selection. Each of the components uses the parameters of the user 305 from the user profile 335 to customize processing for that user. Signal processing is extraction or transformation of the bio-signal data. For example, it processes the bio-signal data to remove unwanted noise and artifacts and/or apply a filter to focus on frequency bands of interest. Feature extraction extracts measurements, variables, and mathematical transformation of measurements of the signal processed bio-signal data. Feature selection selects the features of the bio-signal data that optimize the accuracy of the user state estimator 325 for predicting the brain state of the user.

The user state estimator 325 predicts the user state of the user based on a prediction model using a combination of the features of the bio-signal data, manual inputs of the user through manual inputs 320, context data from the context logic 310 (for example what content is being present by the VR Application 315), and the user profile from the user profile 335. The user state of the user includes the brain state of the user and other states of the user such as head/eye gaze direction. Where the prediction was incorrect, for example, as per user manual input, the data mining improver 330 retrains the prediction model or adapts it based on manual inputs from the user. The data mining improver 330 may also initialize the prediction model for a new user that has no previous history with the system based on aggregate of other users' data.

The data mining improver 330 further may use previous VR sessions to add new labelled data which is used to create a new prediction model or adapt an existing prediction model in the user state estimator 325. The parameters of the new prediction model are stored in the user profile 335 of that user.

The context logic 310 analyzes and determines what the user is doing using manual input 320 of the user and user state estimator 345 (example direction of eye gaze). Also the context of the VR environment that the user is in is supplied by the VR application 315. The context is used as an additional feature and or label of the biological features, for example a truck suddenly appears, used by the data mining improver 330 to update the prediction model in the user state estimator 325. The direction, location or orientation of the user 305 or other data from tracker 145 or sensors 120, 130 may also provide input to context logic 310 to determine context of the VR environment, such as, for example, the position of the truck relative to the user 305 within the VR environment or the orientation or eye gaze of the user 305 relative to the truck within the VR environment.

Figure 4:
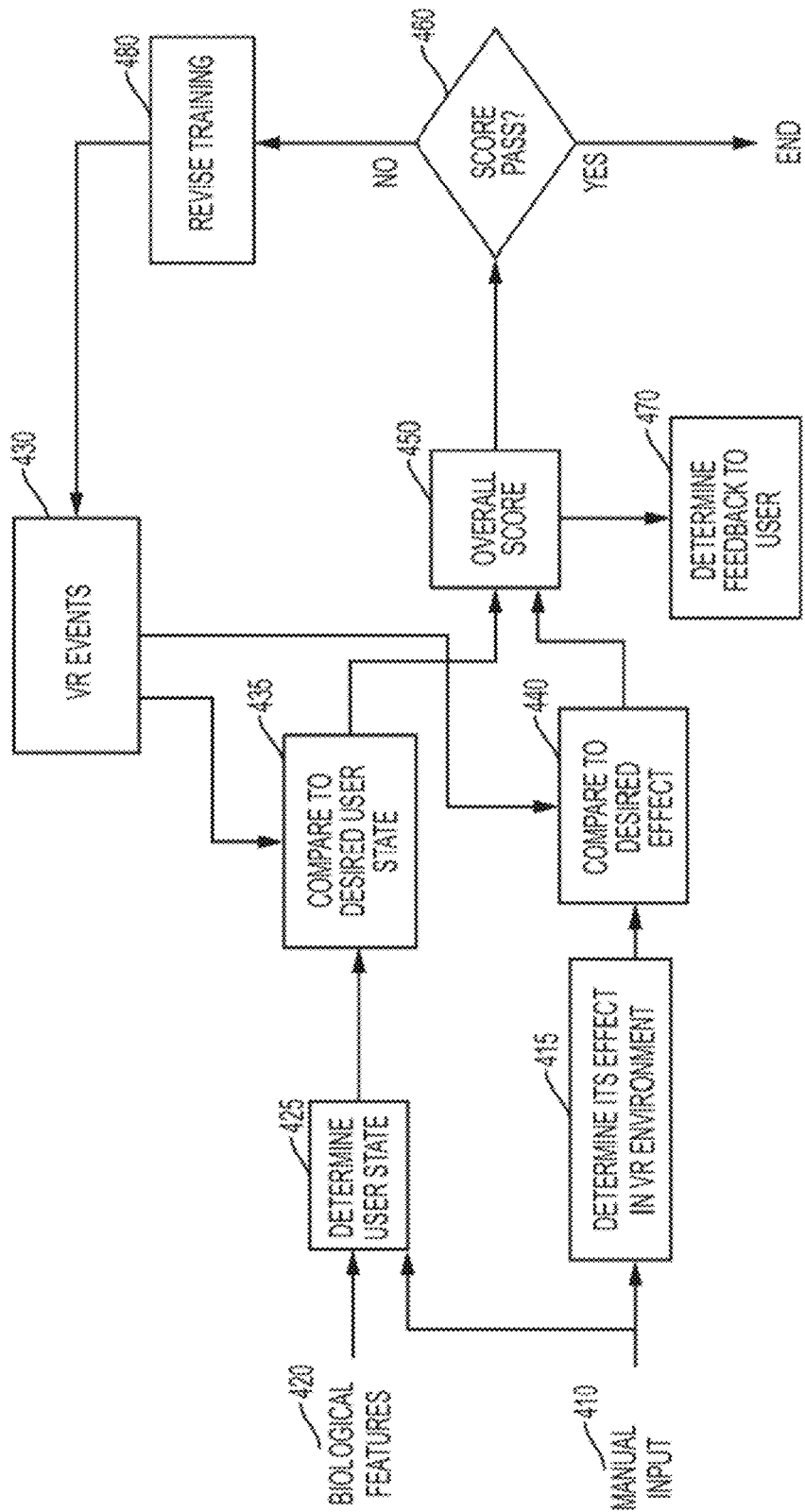
FIG. 4 is a flow diagram of an implementation of a process that may be used to implement aspects of the systems of FIG. 1, FIG. 2 and FIG. 3 according to some embodiments.

Referring to FIG. 4 there is shown a flow diagram of a process for implementing aspects of FIG. 1, FIG. 2 and FIG. 3 where the training system 100 has the user 305 wearing the wearable device 105. The process may involve various operations that may control devices and content display. The trainee or user 305 is, for example, driving a car in a training VR environment. The user 305 enters manual input 410 such as those from steering wheel, gas, and brakes; while the user's 305 biological features 420, such as brain waves and eye gaze direction data, are sensed by the sensors 120 and 130. The biological features 420 and manual input 410 are used to determine user state 425. The user state 425 and the desired user state 435 optionally may only include brain states and not include the manual input 410. The manual input 410 is further used to determine its effect in VR environment 415. The effect in the VR environment 415 is used by the VR application 315 to change aspects of the VR environment accordingly. The VR environment is interactive as it changes depending on manual input 410 and user state 425. Other inputs may also cause effect in the VR environment to provide additional interactivity.

The VR application 315 is presenting a stream of content to the user 305 thereby creating the VR environment. In the VR environment, there are VR events 430 such as: scenario (a) a truck in the oncoming traffic; scenario (b) the truck wavering in the oncoming traffic; and scenario (c) the truck in the oncoming traffic moving into lane of the user's 305 car. For each of these example VR events 430; a score 450 (or grade) is generated based on a comparison of the user state 425 during the VR event to desired user state 435, and the effect in VR environment 415 (or manual input 410) to desired effect 440. Higher scores 450, indicating better user 305 performance, are generated when there is a better match between the determined user state 425 and desired user state 435, and the determined effect 415 and desired effect 440. VR events may be events that occur within the VR environment such as the presentation of specific content to the user within the VR environment, sounds provided by output devices, video displayed, tactile feedback, changes in the user's environment such as temperature, humidity, actions by the user within the VR environment, and so on.

Where the user 305 reached a certain threshold 460 score 450, this training or VR environment ends, but optionally it may also continue for the user 305 to improve. The user 305 is provided with feedback 470 on events where the user 305 may improve such as the user 305 freezes in scenario (c)

when the truck moves into the user's 305 car lane. The feedback 470 is further interpreted by revise training 480 used by the VR application 315 to emphasize or change VR events 430 to customize the training for the user 305 to improve the user's score 450. The user 305 optionally repeats the training content from the VR Application 315 until the user 305 passes the threshold score 460 and/or until the user 305 is satisfied with his or her performance. The feedback 470 may be provided to the user 305 on the display 110 or 225 after the presentation of the content and may include a user state score and effects score over the course of the each of the VR events i.e. post viewing of the streamed VR events synchronized with user manual inputs and user states.

The feedback 470 to user 305 optionally may be provided in real time or near real time to the user 305 while the content is being streamed for the VR environment. This real time feedback 470 is given when the user state 425 (or the effect 415) deviates from the desired user state 435 (or desired effect 440), for example, as a sound through the sound generator 140 and/or a visual indicator in the VR environment being presented to the user 305. The feedback may be provided in real time or near real time during the VR event. The feedback may have additional effects in the VR environment to update or modify the stream of content.

For VR events 430, there are associated desired user states 435. The user state 425 and desired user states 435, for example, can be a label (e.g. drowsy), ordinal (e.g. high drowsy) or numerical (e.g. 0.78 probability of being drowsy). For one VR event 430 over a period of time (specific VR event), there can be, for example, different user states 425 over that period of time. Further, the user states 425 may be a statistical distribution of user states for a specific VR event. The statistical distribution may also have a threshold which for example can be associated with pass or fail for the specific VR event 430. The user state is compared to the desired distribution of brain state for that VR event and a user state score is determined. In one implementation the distribution may be a gaussian distribution and the score is the number of standard deviations of user state from the mean of the distribution. A user state score is the output of the compare between the user state 425 to the desired user state 435; the distribution can be, for example, a label ordinal (e.g. high) or numerical. The user state score is the brain state score where the user state data is brain state data.

For VR events 430, there are associated desired effects 440. The effect in VR environment 415 is controlled by the manual input 410 for scoring purposes, but different manual inputs 410 may create the same effect in VR environment 415 (for example, turning the car a later time but at a greater steering angle). The effect in VR environment 415 and desired effects 440, for example, can be a label (e.g. slowing), ordinal (e.g. low speed) or numerical (e.g. 0.46 probability of slowing down). For one VR event 430 over a period of time (specific VR event), there can be, for example, different effect in VR environment 415 over that period of time. Further, the desired effects 440 and the effect in VR environment 415 may be a statistical distribution of effects for a specific VR event. The statistical distribution may also have a threshold which for example can be associated with pass or fail for the specific VR event 430. The effects are compared to the distribution of effects for that VR event and a performance score is determined. In one implementation the distribution may be a gaussian distribution and the score is the number of standard deviations of effect in VR environment 415 from the mean of the distribution of desired effect. A performance score is the output of the compare of the effect 415 to the desired effect 440; the distribution can be, for example, a label ordinal (e.g. high) or numerical.

The score 450 is a combination of user state score and performance score to provide a combined, for example, numerical score and constructive feedback to the user specific to the content of the VR Application for which he or she is being trained.

VR events 430 are associated with biological signals 340 because both share common timestamps through the context logic 310. This allows analysis of the biological signal 340 relative to a VR event 430. In one example, the VR event 430 can be a label for the biological signal stream 340 which can be used by the data mining improver 330 to create prediction models for the user state estimator 325. The time of a VR event 430 can be associated with an interval of time within a biological signal which can be labelled for machine learning or for the data mining improver 330. In one example, let us say that the time of a VR event 430 occurred at $t_{vr1}$. As an example, an interval in the stream of biological signals 340 is chosen prior to $t_{vr1}$ and after $t_{vr1}$, e.g. the interval can run from $t_{vr1}-200$ ms $_{to}$ $t_{vr1}+1000$ ms. The length of the interval is chosen based on the expected physiological response of biological systems within the body and varies for different systems and stimulus/response physiology. Also the time before the stimulus is important to analyze as this provides a baseline to understand the impact of the VR event 430 on the user's user state. The VR event 430 can be considered as a stimulus and the biological signals are associated with the user's user state 425 or in other words their response to the VR event 430. Event Related Potential (ERP) are signals seen in a user's brain signals in response to a stimulus such as an external audio-visual event. EEG can be used to infer a user's brain state to a VR event using event related synchronization or desynchronization, event related potentials, asymmetry across hemispheres, coherence across a set of electrodes, and power in specific frequency bands. EMG can be used to determine a user's level of muscular tension, their movement in time. ECG can be used to infer the level of a user's arousal. These biological features calculated by the biological signal processing pipeline 345 can be correlated to VR events 430 and are used by the user state estimator 325 along with other features extracted by 345 to estimate a user state 425. These features of the biological signals provide a rich set of information for the data mining improver 330 to increase the accuracy of the prediction models of user state 425.

Referring to FIG. 5 there is shown exemplary implementations of determine feedback 470 in Tables 5A and 5B. Table 5A is look up table that has three columns: the first column is the user state score, the second column is the performance score and the third column is the feedback 470 given to the user and/or instructor associated with those scores. As an example, if the user state score is low and the performance score is low then the feedback is for the threshold 460 to not pass the user 305 and, optionally, to send the user 305 back to re-do the contents of the VR application 315. If the user state score is low but the performance score is high then the feedback to the user is to take a revised 480 training where the content of the VR Application 315 is revised to include, for example, more of the specific VR events 430 for which the user 305 is weak within the interactive VR environment. In another example, if the user state score is low due to high anxiety then a specific VR event 430 may be included to provide meditation training. For mediation training, VR events 430 are set up to reward the user 305 for attaining a meditative state, and also give error signals to the user 305 if they are falling out of the desired meditative state. If the user state score is high but the performance score is low then the user 305 can be given VR events 430 within the interactive VR environment that can help him improve his technical knowledge. If both the user state and performance score is high then the feedback to the user 305 may be pass this VR event and the user can move on to the next sequence of content in the VR Application 315 in a training program. Table 5B is a look up table for determining user state score and performance score. Other scoring techniques may be used and this is an example illustrative example embodiment. This is an example of training a truck driver who is in a car (as part of the VR environment) travelling down the left lane of a highway. There may be a large 18 wheeler truck ahead (an example VR event as part of the VR environment) that is the source of a number of VR events posing challenges to the driver under the training.

The user states 425 and desired user states 435 may compromise a large number of different brain states. Some exemplary brain user states are ability of operator to learn; ability of operator to correctly predict accuracy of their decisions; ability for emotional regulation; concentration; focus; sensory clarity; equanimity; mental workload; sensitivity to relevant external data; insensitivity to irrelevant external data; prior emotional states before performing; and event related potentials in response to stimulus.

The score 450 can further include, for example, the following three types of scores: 1) ability of operator to learn 2) ability of operator to correctly predict accuracy of their decisions and 3) emotional state leading to impaired thinking.

The ability of operator to learn is an innate ability of the operator. High levels of frontal alpha (an EEG signal) are associated with increased learning performance. This can be used to determine if the operator is qualified for the position because there is an expectation of constant learning in these types of jobs.

The ability of operator to correctly predict accuracy of their decisions is the difference in the operator's expectation of his/her error and the correct decision is known as prediction error. Prediction error can be measured from the operator's EEG. So if an operator expected that he/she made the correct decision but the system informed them that their decision was wrong would produce a large prediction error. As an illustrative example, there may be two systems of thinking: System 1 and System 2: System 1: Fast, automatic, frequent, emotional, stereotypic, subconscious; and System 2: Slow, effortful, infrequent, logical, calculating, conscious. System 2 thinking may be less prone to error. System 1 thinking may be based on gut reaction or hunches. System 1 thinking may lead to unreliable decisions.

The ability for emotional regulation are desirable emotional states that enhance critical thinking in a stressful situation. Undesirable states occur for example in what may be referred to as an emotional hijacking where decisions may be driven by primitive response mechanisms," such as when a center in the limbic brain proclaims an emergency and indicates its urgency to the rest of the brain. This may happen before the neo-cortex has an opportunity to glimpse or appreciate the emergency.

Figure 6:
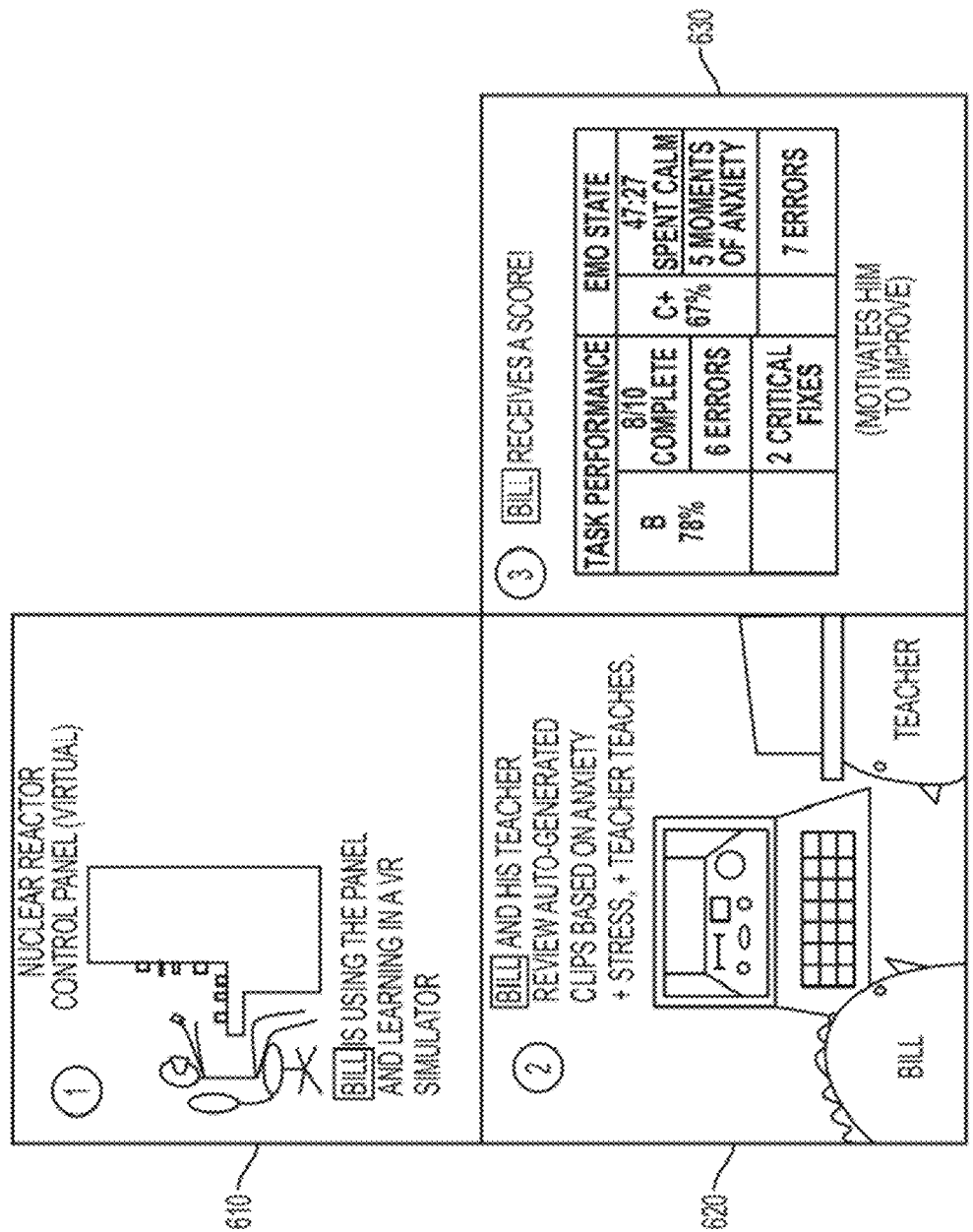
FIG. 6 illustrates a side view of an exemplary application according to some embodiments.

Referring to FIG. 6, there is shown a side view of another exemplary application of embodiments described herein. The training system 100 may be applied to training of an operator in a VR simulation (VR Application 315) of a nuclear reactor control panel. The user may be referred to as "Bill" for this illustrative example. Bill is in charge of operating a nuclear reactor. As part of his training, Bill enters a training simulator (training system 100) that shows him how to use the controls at the reactor. The training simulator works through the wearable device 105. In the simulator, Bill plays through several scenarios 610 (content of VR Application 315) to evaluate his stress levels. Essentially, Bill is practising or training for the moment that something dangerous happens to the reactor, because the sequence for shutting down or drawing down the reactor is complicated. As Bill plays through multiple scenarios generated as VR events within the interactive VR environment, the system logs his Brain State responses (user states 425) during the VR events. Bill's employers and supervisors learn when he experiences stress, because the system has logged his responses 620 as feedback. The feedback may also be provided to Bill within the VR environment in some examples. With this information, Bill's supervisors can also talk over his anxieties with him, and emphasize certain areas of training. Bill becomes a more effective and confident employee. The next time the reactor experiences an anomaly, Bill may not panic and may know how to deal with the problem effectively.

In other words, video clips (VR content) of high stress may be highlighted. Bill is scored on task performance (performance score) and emotional state (user state score) 630. Teachers can also see the VR content and user's reaction in real time or near real time on another display. A video of Bill's simulation is tagged with emotionally charged or stressful points in the simulation of the VR environment (e.g. VR events) so they can also be reviewed off-line with the user.

The training system 100 with the user 305 wearing the wearable device 105 may be used for a wide range of applications. Various applications of the system according to some embodiments are now described. These applications are merely exemplary implementations. Any feature or functionality expressed or implied in the respective applications is not intended to limit the scope of the embodiments. Similarly, various combinations of the applications described herein may be possible.

Helping Children Prepare for an Operation

This scenario focuses on children's needs. In this user story, a child who is scared of an upcoming procedure (such a trip to the dentist, a flu shot, allergy shots, or a surgical procedure) can be taken through the experience of the process as part of the interactive VR environment in advance to ease fears prior to the operation itself. For example, Johnny is scared to get his open-heart surgery next month at a major children's hospital. Johnny's heart surgeon suggests that he play a game in the training system 100 as part of the interactive VR environment, so he can prepare himself mentally for the surgery. This is a new part of the mental health care regimen for incoming patients. It can be administered to patients who live at a distance from the hospital. Johnny is told that it's a virtual surgery "game." Johnny (user 305) walks through the surgery theatre or covers his eyes with a display of the wearable device (as example VR environments) and learns what each tool does, and why he needs the surgery through interactions with the VR environment. He knows the name of everything when he's finished, because he's answered special quizzes and tests about the material. He's played a bunch of games in the space that introduce him to what's about to happen. The game actually replicates the specific hospital environment, so that by the time he enters the hospital, he is more comfortable and familiar, already knows where the bathrooms are located, the environment seems less foreign or threatening and knows how to ask for help from nurses. Johnny's responses (i.e. user state and, in particular, brain state) to these VR events 430 (e.g. games, interactions with tools and other aspects of the surgery within the VR environment) generate Johnny's score 450. The training system 100 can recognize which aspect of the procedure creates the most stress for Johnny through the score 450 and provides feedback 470 as part of the VR environment and during the VR events, in some example embodiments. In some examples, the system may possibly revise the VR environment 480 for additional VR events 430 that can help Johnny be more comfortable. When Johnny's score 450 reaches a certain threshold 460, he may be better prepared for his upcoming procedure.

Social Awareness Community

Many games and VR experiences rely on clumsy, inaccurate models of emotion, and don't create clear channels of communication between players or users, much less between players and characters and the user state. In this system, users experience a world where artificial characters or anonymous players (examples of content within the VR environment) respond to their emotions and thoughts in an honest way, based on data from the system of the present invention. Self-awareness is important to the process of therapy, and a component of the feedback provided by the system according to some embodiments. For example, Walt (a user) is in treatment for an anger management issue. He is the type of person who compartmentalizes his anger until it explodes, rather than expressing it honestly. His therapist suggests that he re-learn how to express his emotions in a VR environment of the training system 100, where characters of the VR environment can react to virtual expressions of his brain state (as example VR events and feedback) and not the way he pretends to feel. Walt uses the training system 100 of the present invention on a regular basis to access this construct (VR environment). The construct may be a casino floor, museum exhibit, shopping centre, bar, public park, or other crowded space. A bunch of agents and characters surround Walt, engaging him in conversation or activity, such as games on the casino floor or in a carnival midway as example VR events. The environment is designed to test Walt's emotions both in a social way and in a stress-based way—when Walt loses games (i.e. VR events 430), he gets angry (i.e. user state 425). The characters respond to Walt's emotional and mental state based on information gathered by the system of the present invention generates his score 450, which may be example feedback during the VR event. While Walt expresses emotion differently in the real world, or hides his feelings, the characters in this world know how he's really feeling based on his EEG information. As Walt wanders and explores this world, the way these characters respond to him as feedback reflects his actual state (i.e. through revise training 480), which he can't hide. When he's sad or negative, they try to cheer him up, or they share their own negative feelings. When he's angry they are fearful of him, or react with hostility to match his own (i.e. lowing his score 450). The feedback 470 is used to revise 480 the VR events 430 which drive the characters and scenarios in the VR environment. When he's cool and calm as determined by his brain state, they come and chat with him, or try to draw him out into a more outgoing and gregarious interaction. When he's excited and positive, they come and dance, or discuss ideas with him. The training system 100 provides feedback 470 to Walt based on his score 450 so that he may then improve his future scores. Optionally, some of the characters may be real users acting through the VR application 315.

Interactive Sensitivity Game

Most sensitivity training in the corporate world relies on perceived affective cues, emotional responses, body language, and other signals that are already difficult for insensitive people to discern or understand. The training system 100 according to some embodiments of the device allows the opportunity to create a VR environment where users learn and practise sensitivity by engaging with characters in the VR environment where they wear their "emotions on their sleeve" (visually represented in real time via colour-coding, auras, icons, logos, avatars, etc.) based on determined user or brain states during VR events within the VR environment. Socially interacting in this world may help train people to look through the surface and see the inner world within people based on feedback. The world is gamified, so that players are rewarded for their ability to spread calmness, ease, happiness, and other positive emotions through social interactivity. The user 305 is scored based on their responses to these VR events 430. For example, Francine (a user) goes into an online VR gaming environment with her head-mounted display and EEG combo (wearable device 105). Francine interacts with all kinds of characters in this world via in-game avatars (VR events 430). Internal EEG-based states are visually overlaid on the avatar so Francine can see the emotional and mental state of the characters in real time, and they can see hers. This is done by animating facial expressions perhaps even exaggerating them in a cartoon-like way with colour enhancement such as red scale for anger, and blue scale for sadness (i.e. revise training 480). By reviewing her score 450 and the feedback 470 from these VR events, Francine may see where she can improve her sensitivity by improving her future scores 450. In addition, Francine's training may be revised 480 based on her feedback 470 such that new scenarios and characters are presented to her as content within the VR environment driven by VR events 430.

Combating Stage Fright

Public speaking can be very challenging for some people. There are courses that specialize in teaching people how to speak in public without fear, but they don't necessarily deal with the realities of social anxiety disorder or other real health care concerns that keep people away from speaking up. This training system 100 may help users develop public speaking and personal skills in a VR environment, wherein the system helps the user deal with feelings of anxiety. It would be beneficial to both people who have anxiety dealing with public speaking, and to the people who are trying to help them, such as employers, therapists, coaches, and friends or family.

For example, Parker (user 305) is the valedictorian of his graduating class, which means he has to give a speech to everyone attending his graduation ceremony. Unfortunately, he is extremely nervous about delivering speeches and presentations in front of large groups in public. He's really scared that he will mess this up in front of his whole family and all his friends. After writing his speech, Parker uses the training system 100 to build or engage a virtual practise space or VR environment where he can practise giving his speech. The space matches the physical environment where he will be delivering the speech: the size of the space, lighting and weather conditions, and how many people will be in attendance, as well as ambient noise like coughing, sneezing, murmuring, or the sound of mobile devices. After building or entering this VR environment using the device, Parker can practise delivering his speech. The VR application 315 tests Parker's ability to handle the stress of giving his speech by responding to his brain state. The speech delivery may be one or more VR events and audience response may also be VR events. If Parker is relaxed, the environment throws him a curveball (VR events 430) and starts some commotion in the virtual audience. Peter's reaction (as determined by his brain state) would be scored. If Parker is nervous (as determined by his brain state), the VR application 315 calms down the audience so he can practise getting through the speech. Depending on how Parker handles the curveballs, i.e. VR events 430 based on his score 450, the virtual audience will have a positive or negative reaction—lots of applause, or not too much applause that are driven by feedback 470 and revised training 480. In some example embodiments, feedback may be provided using VR events that react or are driven by the user state.

Customer Service Training

Many employee training modules rely on videos, role playing, or simple pencil-and-paper quizzes, or basic computer quizzes. This training system 100 would allow businesses to train employees to deal with difficult customers using a VR environment, brain state monitoring, and feedback rather than relying on self-reporting of emotional states and other traditional training techniques. Further, it would generate feedback data on difficult situations that would help other employers and employees understand the challenges of dealing with the general public.

For example, Dante (user 305) just got a job at a major convenience store chain. The chain prides itself on delivering the same quality of service at each of its stores. Part of his job training is learning how to deal with difficult customers. While wearing a wearable device 105, Dante plays out several scenarios of difficult customers as VR events. This includes a few different scenarios of mugging and shoplifting. The system simulates different customer behaviour (VR events 430) depending on the system's evaluation of Dante's stress, calm or levels of frustration level (for example user state 425 versus desired user state 435). As he gives in to frustration, the customers get tougher (feedback or VR events). When he's able to calm his mind and focus (desired brain state), the customers grow easier to deal with and eventually leave (additional feedback and VR events). Dante is rewarded by pleasant customers (feedback or VR events) when the system detects he is calm and is greeted by difficult customers (feedback or VR events) if an undesirable brain state is detected. Over time, Dante learns that the way to deal with tough customers is to focus his mind and maintain a sense of calm, and also thereby increasing his score 450. And if Dante is struggling based on his score 450 and feedback 470, then different VR events 430 are revised 480 such as meditation practice to help Dante improve his equanimity.

Virtual Therapy Space

Post-traumatic stress disorder ("PTSD") is an increasing problem. Soldiers, law enforcement officers, survivors of domestic violence, and even those who have been serially harassed by bullies and classmates can experience it—even years after the initial trauma. But most therapies for patients with PTSD focus purely on cognitive behavioural therapy, without an immersive or sensual element. This training system 100 helps patients with PTSD identify and learn how to deal with triggers (VR events) in a safe VR environment. It is just immersive enough to create the necessary feelings that need to be processed for healing, but that immersion happens in a space the patient actually chooses.

For example, Oliver (user 305) is experiencing PTSD after a tour with the armed forces overseas. Oliver sometimes enters fugue states or experiences rages or crying jags that he can't explain. He doesn't know what triggers these events. As part of his therapy to deal with PTSD, he enters a VR environment that emulates the places where he experienced trauma as different VR events. He wears a wearable device 105 to access this VR environment and score his brain states during VR events. While wearing the device 105, the device can read his inputs and determine his brain state during the VR events. As his anxiety increases, the device takes note of the change in baseline brain state and generates a score 450 with feedback 470 with a timestamp at the time of the VR event 430, so Oliver and his therapist can determine what VR events exactly made him so anxious. Over time, Oliver identifies what triggers his emotional responses, whether it's a loud noise or flashing lights or even a certain colour. In the VR environment, Oliver is able to expose himself to this stimuli (VR events) in a safe way, and learn how to deal with the stimuli on his own (i.e. user state 425 versus desired user state 435), without over-reacting. His score 450 and feedback 470 would a guide on his improvements with time.

Improve Golf Performance

Many coaches can tell an athlete to get in "the zone." Fewer of those coaches have access to direct brain-state data about whether an athlete is actually in that zone. The system according to some embodiments uses brain state data to help athletes and casual players perform better or nail a specific technique. For example, Geoff (a user) wants to improve his golf swing. He enters a VR "golf coaching" environment—a golf course is simulated using VR technology. The VR headset (wearable device 105) also contains EEG sensors. Geoff tees up and practices his swing in the VR environment. As he get ready to swing (a VR event), EEG data is being collected. This data is used to overlay mindfulness information, i.e. VR event 430, or feedback, on the training scenario. For example, if Geoff is relaxed and focused, the image of the golf club will glow green; if he is distracted, it will glow red. The glow and color is an example of real time or near real time feedback during the VR event. Geoff can also enter into a "mini-mindfulness mode" to refocus himself before he takes a swing. Geoff then swings the club when he reaches the ideal focus level. The club is embedded with sensors so the VR training program, i.e. sequence of VR events, can determine if optimal swing positioning, etc. (manual input 320), is being achieved. After the swing (i.e. manual input 410), data corresponding to Geoff's performance is displayed in his VR environment—i.e. how far the ball travelled, effect of wind, etc. by effect in VR environment 415. The training system 100 presents Geoff with his score 450 along with his user state 425 and desired user state 435 as part of the feedback 470 showing both mentally and physically he may improve his performance for next time. A training program implemented by the wearable device may be a sequence of VR events where the sequence of VR events may dynamically change to provide feedback in response to a user's scored brain state.

Another Example Application

In accordance with another exemplary embodiment, more than one copy of the training system 100 of FIG. 1 may be interconnected together, via the other computing device 160, to create a VR environment for more than one user to provide virtual interaction between users. FIGS. 1 to 5 are accordingly modified for this other exemplary embodiment. This other exemplary embodiment is applied in some of the scenarios as an illustrative example.

Other Scenarios

Figure 7:
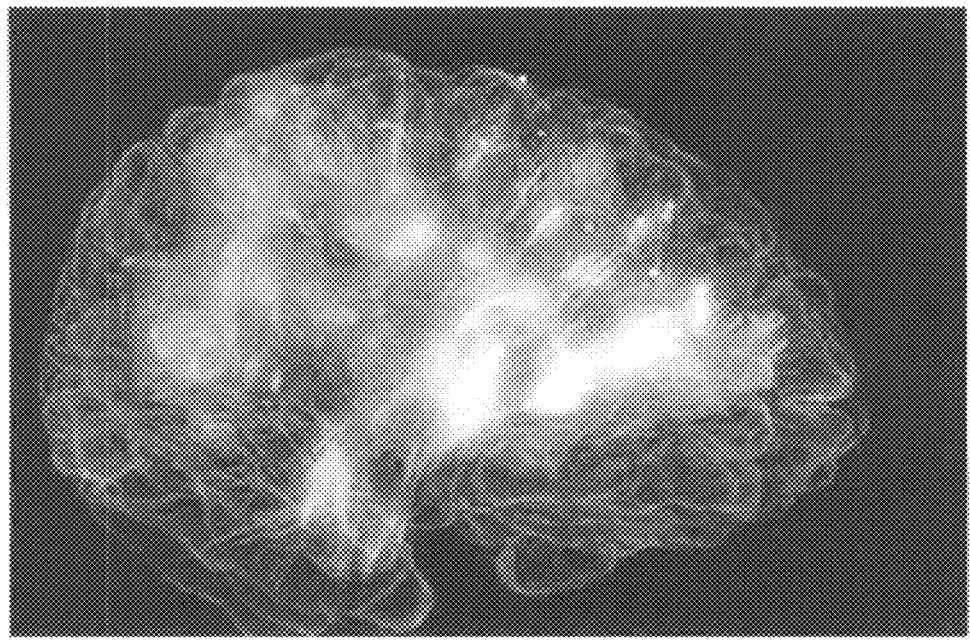
FIG. 7 shows an example visual representation of content and/or feedback relating to 3D brain activity in a VR environment according to some embodiments.

FIG. 7 shows an example visual representation 700 of content and/or feedback relating to 3D brain activity in a VR environment according to some embodiments. This illustrates an example of what a visual representation 700 of 3D brain activity may look like in a VR environment to provide a visualization of feedback to the user within the VR environment. Embodiments described herein may be used for applications that utilize real-time 3D visualization of the brain activity as feedback or indication of the user's brain state. The VR display may show spatial activity in the brain and in the body (e.g. look around to see inside your mind and in your body in real-time). This may be useful for biofeedback and psychotherapy. Neuro-feedback may be location-specific. This type of highly specific training can be hard for a user to engage with because it is so difficult to learn the relation between auditory stimulus and state of mind. VR visualization of feedback may help the user learn the connection as well as techniques for engaging target areas.

Figure 8:
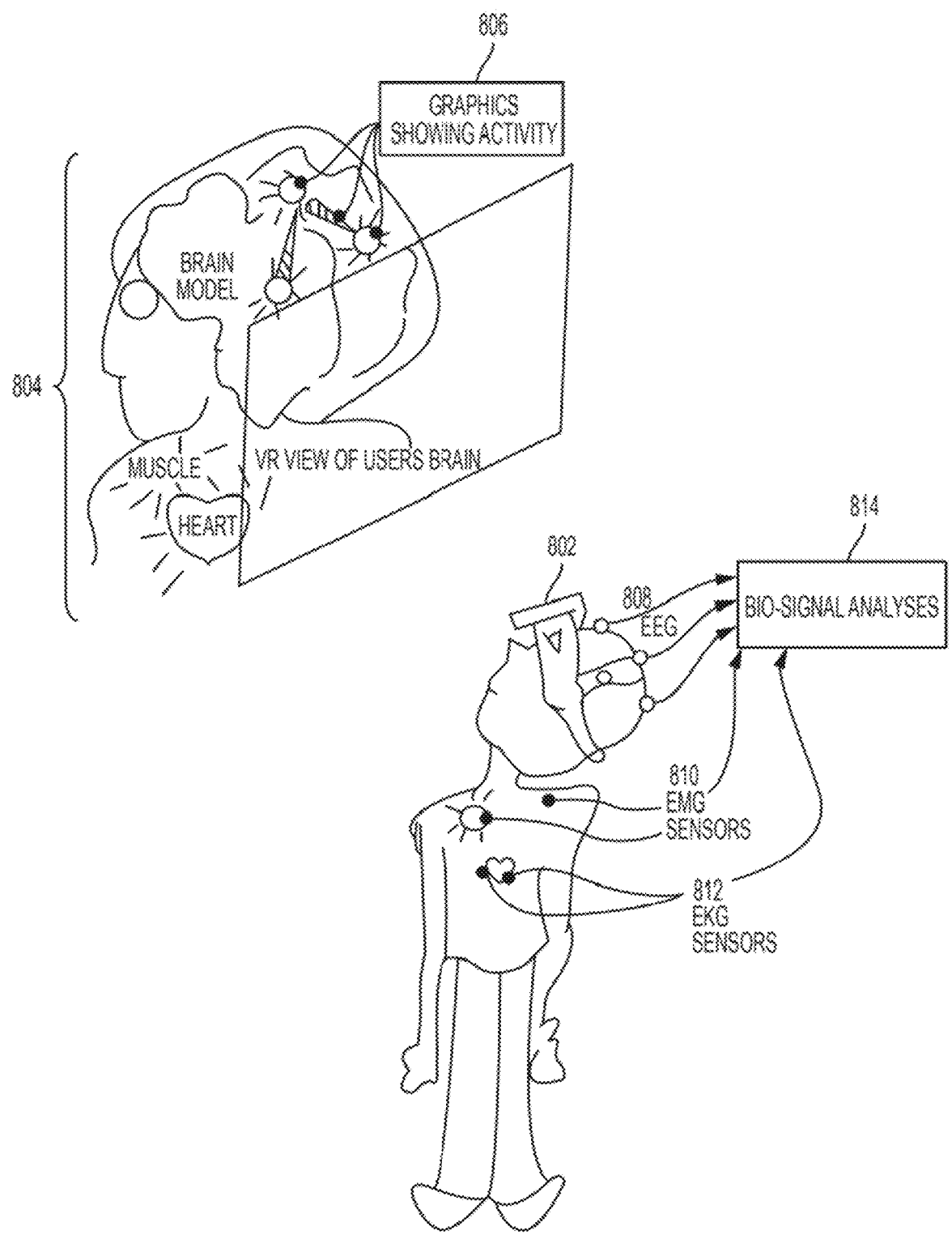
FIG. 8 illustrates an example of a user interaction with the training system according to some embodiments.

FIG. 8 illustrates an example of a user interaction with the training system 100 to provide a visual representation 804 of inside the user's mind using a VR environment rendered on the stereoscopic display. The example schematic illustrates a wearable device 802 with bio-signal sensors 808, 810, 812 that provides visual representation 804 or content in a VR environment. The visual representation 804 may provide a VR rendered view of the user's brain with graphics showing brain activity depicting determine brain states. The bio-signal sensors 808, 810, 812 provide bio-signal data to a device or processor 814 implementing bio-signal processing operations as described herein to determine brain or user states, which are in turn used to determine a user state score and provide feedback as part of the visual representation 804 in the VR environment.

Figure 9:
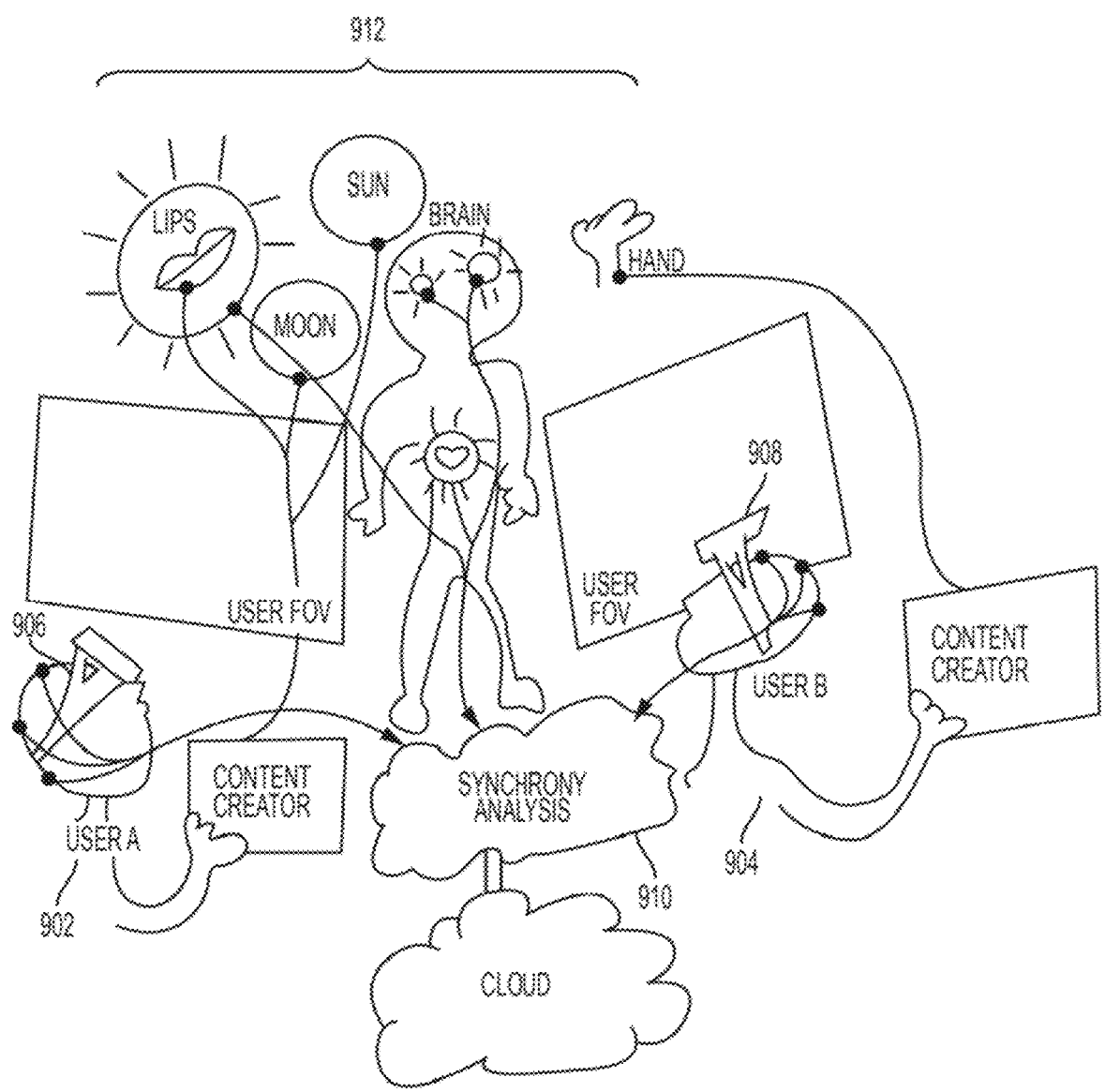
FIG. 9 shows an exemplary application for fostering an emotional connection in a VR environment according to some embodiments.

FIG. 9 shows an exemplary application for fostering an emotional connection in a VR environment. As an illustrative example, the application may involve two users 902, 904 each with a wearable device 906, 908 with bio-signal sensors to provide bio-signal data to a device 910 implementing a synchrony analysis process to synchronize and link the bio-signal data from the two users 902, 904. A real time or near real time 3D visualization of a mental and physical state (an example visual representation of feedback) can be extended to seeing inside someone else's body (e.g. use it for two person interactions), to see inside someone else's brain as they see inside yours. A visual representation 912 in the VR environment may illustrate a collage of the two user brain states (provided as output from device 910). The visual representation 912 may be displayed as additional feedback and/or content in the VR environment. Analysis of cross-state such as neural synchrony may be provided as output from device 910 and displayed as the visual representation 912 in the VR environment. This may be useful to increase intimacy between users 902, 904. Each user 902, 904 may have a different field of view (FOV) of the visual representation 912 and a user 902, 904 may see the same or different content as the other user 902, 904 in the VR environment. Users can work to synchronize with each other based on the feedback display in the VR environment. It can be augmented with other imagery that the user can manually effect to intensify feelings and facilitate new types of telecommunication.

Figure 10:
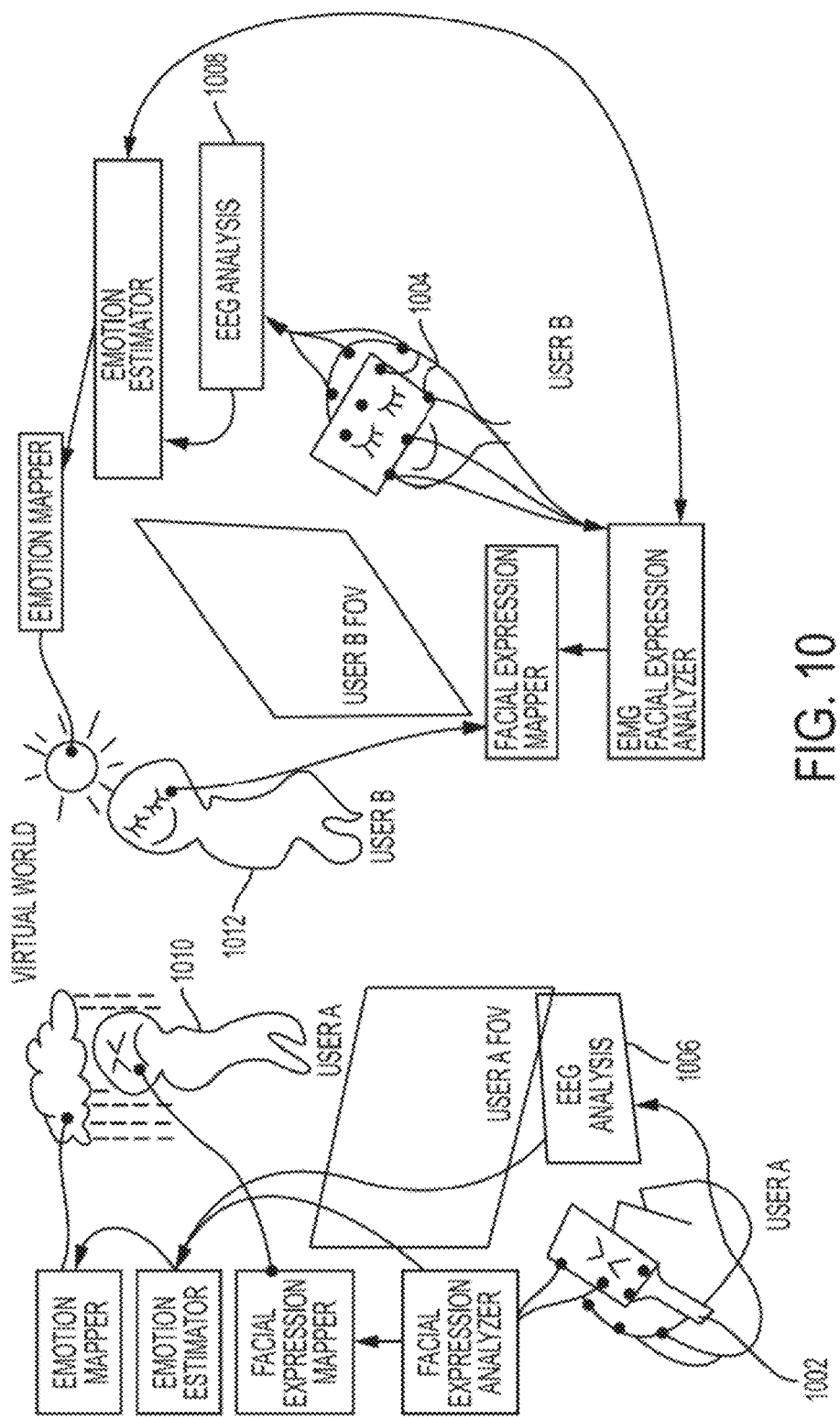
FIG. 10 shows an exemplary application for representing emotional avatars in a VR environment according to some embodiments.

FIG. 10 shows an exemplary application for representing emotional avatars 1010, 1012 in a VR environment according to some embodiments. The visual representation may represent emotional avatars in a VR environment as different VR events or types of feedback. Each user may have a wearable device 1002, 1004 with bio-signal sensors to provide bio-signal data to a device 1006, 1008 configured to generate a user state score, as described herein. The device 1006, 1008 may implement different operations such as EEG analysis, emotion estimation, emotion mapping, facial expression mapping, and facial expression analysis. The device 1006, 1008 may include one or more processors configured to implement the various operations. The device 1006, 1008 may serve one or more wearable devices 1002, 1004. Adventures or activities with others may be more interesting if people can see how the other person is feeling by way of a visual representation in the VR environment. The usage of the facial sensors (an example of bio-signal sensors of wearable device 1002, 1004) may allow for the mapping of a user's expression to the face of their avatar 1010, 1012 in a VR environment (e.g. to represent detected facial states with associated smiles, squints, winks, furrows, frowns, etc.). This can be augmented with brain signals from wearable device 1002, 1004 to do emotion estimation by device 1008, 1006. This estimate can further augment a characters appearance in the VR environment as an example of feedback. A positive effect could be rendered as warm colours. A negative effect could be rendered as cool colours. When users are excited they could spout rainbows. This may form the basis for emotional gaming. An objective in this example application may be to evoke emotions in others as VR events in a virtual world. Emotional state estimation can also facilitate single player storytelling, when the story knows that you are scared for instance and the environment could alter to intensify the feeling. Different users may have different FOV of the VR environment.

Figure 11:
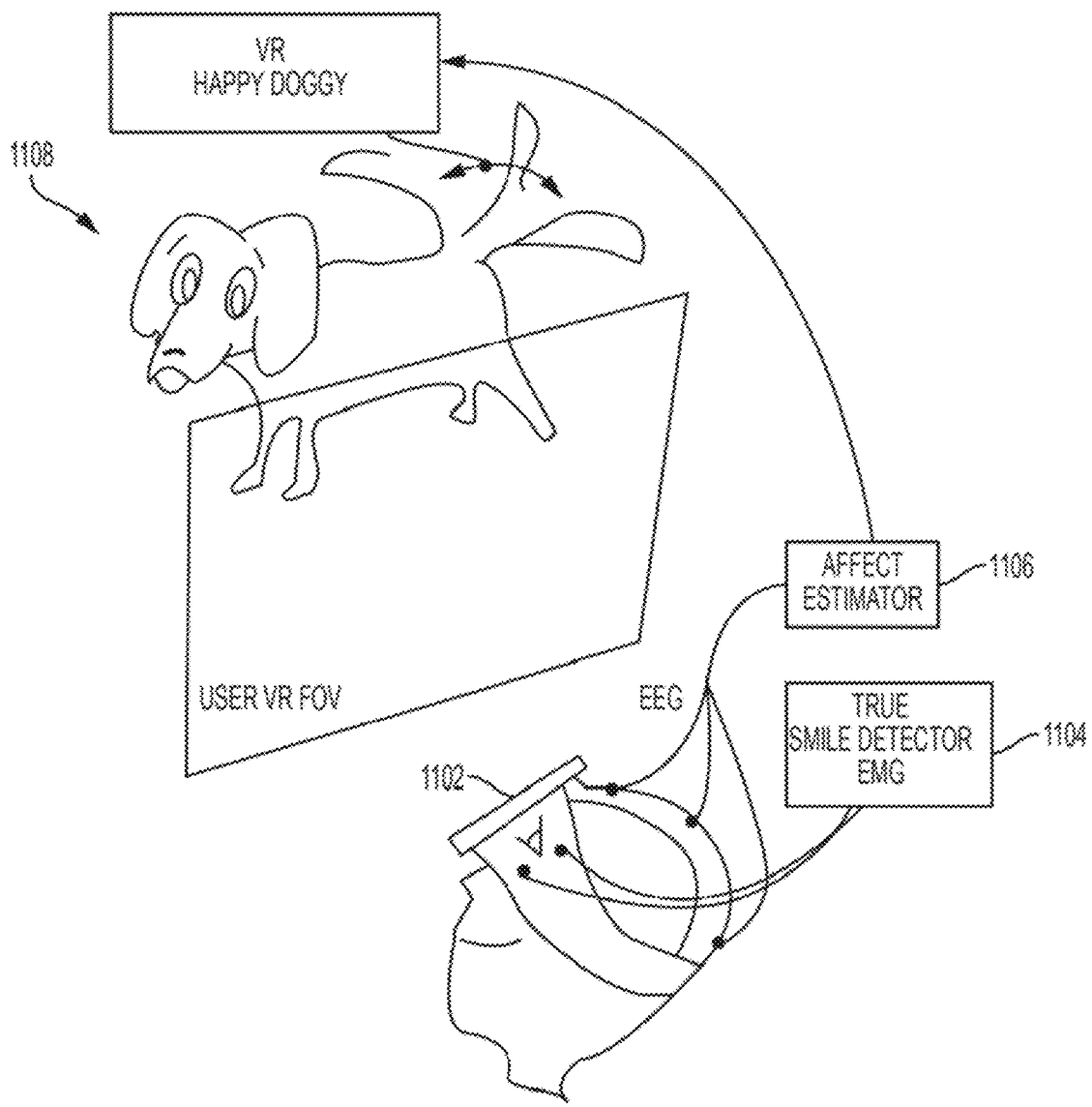
FIG. 11 shows an exemplary application for a therapeutic VR pet according to some embodiments.

FIG. 11 shows an exemplary application for a therapeutic visual representation 1108 of a VR pet in a VR environment according to some embodiments. A wearable device 1102 has bio-signal sensors to provide bio-signal data for true smile detection operation 1104 and a affect estimator operation 1106 (implemented by the wearable device 1102 or another device connected thereto). It also allows for single player emotional gaming which might be optimized for therapeutic use. For example, a VR pet that reacts well to true moments of user happiness, or games when success is linked to cultivating different emotional states. The visual representation 1108 may update based on the user state score to provide feedback to the user.

Application: Entertainment—Calming Environment Uses EEG to Respond/Navigate

Embodiments described herein may use improved controllers to navigate space in some examples. The navigation within the VR environment may be an example of feedback based on the user state score. Using vision and focus/attention in the wearable computing device 1202 could allow someone to orient and focus to move, and still keep the experience moving and responding even without intention, revealing new elements. This would create a new way of interacting with and controlling VR environments based on brainwaves to provide effects within the VR environment as content and/or feedback based on the user state score. For example, Bill enters a virtual world designed for exploration and experience via a wearable computing device. Rather than using a handheld controller, he determines his velocity in 3D-space by his focus/surprise/noticing his environment. Instead of an easy feeling of control, the environment seems to take him around and respond to his brain states in real time as example feedback based on his scored brain state. Bill gets bored of flying around the space, and as he loses attention and relaxes, aspects of the VR environment change, and his motion and velocity drastically slow down.

Bill gets interested by this change, and notices an engaging aspect of the VR environment. His new level of attention and gaze orientation navigate him toward that element of the VR environment (which may be an example VR event) automatically.

The system may permit a range of inputs that together provide greater responsiveness, effects in the VR environment, feedback or a combination thereof, including brain state inputs and other inputs in combination, for example: 1) noticing something salient, 2) focus, 3) attention, 4) head orientation, and 5) eye gaze. In this example, these inputs are processed by the VR system, and the output may include 1) an environmental response, 2) the user's position in the simulated 3D space, and 3) the user's velocity. In this example, a participant may have a wearable device 1202 with bio-signal sensors and a display to provide a VR environment with a participant view 1208. A researcher may have a device 1210 with a display to provide a researcher view 1204, 1206 that may update or modify based on the user state score of the participant to provide feedback to the participant and/or researcher.

Application: Entertainment—Virtual Tourist

Embodiments described herein may be used to implement an immersive virtual experience, based on brain-state data gathered in real time from the wearable computing device 105. Unlike current virtual reality systems that rely on a command-control system that is frequently hand-held, this one responds interactively based on data generated by changes in the user's brain. For example, Janice wants very much to go to Paris. She downloads an immersive experience map of the city for use on the system which may be provided as part of the VR environment. Janice enters her map of "virtual" Paris to relax. Depending on her mood, emotion, or cognitive load, different layers of information appear on her "tour" of the city as part of the VR environment. Janice wanders around Paris and enjoys photorealistic sights and amazing sound quality. As she gets a little less engaged with the sensory experience over time, information about the things she's seeing is overlaid on the screen (history and physical attributes of buildings, cultural references, etc.) As she gets bored, typical Parisian events start to happen in the virtual world (a street performer calls out, a couple kisses, etc.). All in all, the experience allows Janice to experience Paris, which is a real place, but in a surreal, engaging, and responsive way.

The system permits a range of inputs: mood, emotion, cognitive load, focus, drowsiness, etc. In this example, the inputs are processed by the VR system, and output may include feedback as: VR Events in the virtual world, Overlaid information in the virtual world.

Application: Data Gathering—Evaluating Audience Engagement with a 3D Environment Embodiments described herein may be useful for someone creating a video game or any kind of 3D world could have the experience validated using brain state data. The present system including a combination of bio-signal sensors with a VR device may allow designers to gather a unique and novel set of data from the user's brain. This combination may allow designers for VR games and experiences to develop experiences that are even more personal and immersive. This is an added value for game designers and experience designers working with VR environments. For example, a video game may be generated for a head-mounted display. To validate the world, users may be tested using a brain-sensor and HMD in combination. Motor areas, emotional areas, focus, attention, vigilance, drowsiness are all used to evaluate the user's engagement with the virtual world and their interest in the game. In addition other biological sensors such as: heart rate, muscle activity, respiration rate, temperature etc. can be used to determine user's level of arousal, stress and other physiological parameters that are correlated to emotional state. The system receives a full report on moments of weakness and moments of strength of the application and uses that to improve the environment. The system also learns that certain types of motions/controls in their world generate emetic responses and feelings of nausea, or other general feelings of discomfort like neck pain, eyestrain, claustrophobia, headaches, ringing ears, etc. The process iteratively continues to improve the environment and motion within to optimize for positive experiences. is the system may be able to release a game that takes a variety of physical responses into account, so that more people can play.

Embodiments described herein may permit such inputs as: a user's motor activity, emotional activity, changes in brain-state, focus, attention, vigilance, drowsiness, nausea, and other responses. The system of the present invention creates such outputs as: raw metrics and data of user interaction, such as movement, changes in focus and attention, changes in wakefulness, and other data that contribute to a portrait of user engagement. This data could then be translated into reports, infographics, and other valuable internal information for creating better experiences.

Application: Entertainment—Experience Sharing and Response Tracking/Shared VR Platform/Photo Sharing for VR Services allow users to share their gaming experiences, but not with added value of real time emotional data. Nor can those services replicate real-world experiences that are actually happening. In this system, users can record experiences and share them with a community, and receive the collective emotional response of viewers back via a shared VR platform similar to photo- and experience-sharing platforms. In effect, this creates a social media platform for the sharing of virtual and emotional data. For example, Birut is on an amazing trip in New Zealand and wants to share the experience. He uses his special panoramic camera to record the experience of a walk along a beautiful cliff side. Birut uploads the content to a shared social virtual reality platform. This platform allows his friends to experience VR environments created based on his camera input data, and annotate those environments with emotional data gleaned from the system. Jim, another user with access to Birut's profile, is able to access the content and experience it as a VR environment via the wearable computing device. As Jim experiences the cliff side walk (VR event), his mental and emotional responses are recorded and scored via the system to provide feedback. A few hundred people experience the cliff side walk, attracted to it by auto-generated notes (examples of feedback or VR events) that others have found it moving, engaging, as detected by their emotional responses via. Users and Birut himself are both able to access the emotional and mental data and see how people are experiencing the cliff side walk. The moment when a bird flies by (another VR event) creates an interesting reaction, where some people are very drawn to that bird, while others simply ignore it. Users can see this clearly in the feedback data associated with the experience. The data shows how a moment where Birut mishandles the camera for a second causes some anger in a group of people. Some percentage of the people start to get bored halfway through the experience and end it, while other stay engaged and persist to the end. Users subscribe to Birut's channel where he is generating quality content.

The system of present invention can collate data from multiple inputs, including the EEG sensors, a camera, a microphone, motion detection, and temperature.

Embodiments described herein can also generate data from EEG input that enhances virtual environments and makes them more attractive to potential viewers. This makes the VR environments and content thereof more participatory and dynamic.

Application: Data Gathering—Discomfort Detection

Contemporary virtual reality technology can create a lot of discomfort for some users. The ability to detect discomfort (i.e. nausea, anxiety, heart rate) while using a VR device, so as to put a stop to bad experiences in the VR environment.

For example, Anne is wearing a head-mounted VR rig. She begins to experience nausea in the environment. Embodiments described herein use EEG sensors to determine that she is experiencing a change in her baseline brain-state. The changes in brain-state that Anne is manifesting match a profile the system has established for physical discomfort. The system sends this data to the VR device. The VR device sends Anne an output (feedback) that helps her check-in with her discomfort. In this scenario, that could be a simple text message in the heads-up display, or even a character in the VR environment who asks if the player or user is feeling well. If the discomfort persists, the VR device offers Anne a way of opting out or ending the experience quickly.

Embodiments described herein allows for multiple inputs from the wearable computing device, including EEG sensors, motion detection, heart rate, eye-tracking, and other data that can help the system determine whether a user is feeling discomfort.

Embodiments described herein can create outputs like text messages, a pause in the gaming or virtual experience, dimmed lighting, changes in transparency and opacity, or even characters who can respond in real time to players/users.

Application: Data Gathering—a Room of One's Own

Designing a VR environment can be a special exercise that creates a meditative mindset. Akin to the "mind palace" idea of cognition, designing special places with an emotional meaning for the user can be a valuable tool for people using virtual reality technology. Re-creating an environment that triggers major emotional changes in the user, such as a childhood bedroom, or a special place in a person's history, or even a museum exhibit.

For example, Virginia has to move to another country for work. She has a very high-stress job. In order to help herself remain productive at work, Virginia creates a virtual meditative space. Virginia slowly builds this space in her VR device by selecting dimensions, colours, and textures. Then she adds in features from photographs and advertising materials. She can even shop online for elements to add to the room, like a fountain or sculpture. Embodiments described herein allows Virginia to move elements of the room, or change their shape or colour, only when she's focused (desired brain state), which may be an example of feedback. This is applying focused attention to the principles of design to enable movement of objects and creation of VR space as different forms of feedback. Slowly, Virginia learns to focus by making and re-making the room as a meditative exercise.

Embodiments described herein can input data from EEG, heart rate, eye-tracking, and other sensor data and translated it into VR maps with responsive changes to colour, music, opacity, transparency, and other elements that help create a more immersive virtual world.

Application: Entrainment—Preventing Boredom During Exercise

Many exercise programs have no way of controlling for when members get bored. This system provides constant stimulation to people during exercise via a VR environment, so that they don't get bored or focus too much on exertion such that it distracts them from accomplishing a goal. This system is engineered to constantly maintain attention away from exertion by providing stimuli or feedback based on changes in brain-state, gathered from EEG sensors in the system.

For example, Liana is trying to exercise more. But she finds it difficult to stick with any one exercise for a prolonged period. At the same time, she doesn't enjoy aerobics or weightlifting classes. One of the trainers at the gym recommends that she use the system to maintain her attention while she is on machines like treadmills and bikes. The wearable computing device provides her with visual stimuli as VR events, based on a suite of available content. She could be in a natural environment, or an urban one, or even a fantasy environment like Middle Earth or a space station. If Liana maintains her heart rate and focus (detected through by the system), the environment stays in place as feedback. If she loses focus or her heart rate, the environment begins to fade away as further feedback. In another embodiment, the greater Liana's engagement gives her additional power to play a game in the VR environment. This takes Liana's mind off the exercise, as she learns more about her fantasy environment or plays a neuro-feedback based game.

Embodiments described herein can translate inputs like heart rate; EEG; eye-tracking; pulse; gyroscope; accelerometer into outputs like dynamic changes to virtual environment based on changes to wearer's brain state, such as changes to music, lighting, tempo, sound effects, colour, activity.

Application: Entrainment—Developing Attentional Bandwidth

Contemporary methods of training students for tests can only offer variations on tests, without any data on how students are focusing. This would help train students and others to develop greater focus and vigilance over prolonged periods of time, with the added benefit of incorporating brain-state data into the mix. With brain-state data, students, parents, teachers, tutors, and counselors can actually have an accurate picture of what helps students engage with the material they are attempting to learn, and how much time they actually need to study.

For example, Dennis has a hard time focusing in class and at home, when doing his homework. Dennis' parents download an app into his wearable computing device according to some embodiments to help him learn how to focus. The application takes a gamified approach to developing attentional bandwidth. It rewards Dennis with extra points and badges as feedback for completing tasks in a calm, focused frame of mind (desired brain state). Sometimes these tasks are timed, but not always. He can choose the types of tasks he would like to perform in the virtual environment: catching butterflies, setting up dominoes, going sailing, etc. Over time, Dennis gains more attentional bandwidth. He is able to focus more intently on the tasks he's been assigned.

Embodiments described herein can track data inputs related to focus and attention, such as EEG sensing, eye-tracking, heart rate, and motion, and translate it into outputs like dynamic changes to a virtual environment, text messages, virtual prompts, and reports on attention.

Application: Entrainment—Developing Attentional Bandwidth in the Classroom

The majority of current testing mechanisms in schools reflect only a certain way of taking tests which is growing increasingly vulnerable to cheating and does not reflect the way students actually learn. The VR system according to some embodiments provides schools and students with alternative testing mechanisms that may be more user-friendly, that also share data on student brain state and performance. This data can then be used to bring up test scores, improve tests, and benefit students and their schools.

For example, the town of East Dillon has students with low test scores across the board. As part of accountability legislation to help students raise test scores, the school enters a pilot program that charts focus and attention among students during tests. The goal is to raise test scores by reducing test anxiety and helping students focus solely on the test, and not on their classmates or the surrounding environment. During tests, students at East Dillon High School put on wearable computing devices of the present invention, and perform their tests in a virtual environment. The test presents as a game (as a sequence of VR events), where students choose different answers from a multiple choice list by clicking, pointing, blinking, or otherwise interacting with the virtual environment. This VR environment has none of the usual distractions of a classroom. It can be quieter and friendlier, with calming sounds and no classmates. As students perform the tests in the virtual environment, the system charts their ability to calm down and focus on the test. The system generates reports (feedback) for students on times when they feel the most anxiety or distraction. This is matched against existing progress reports, academic calendars, and other personal and health data. Students and parents can see how students are really feeling as they perform during tests. These reports can be used to talk with counselors, therapists, or academic advisors to help refine study techniques. Having learned how to calm down during tests, students can focus better on major tests like the PSAT and SAT, or during state-wide tests.

Embodiments described herein can take inputs such as EEG data, eye-tracking, and motion-detection and translate it into outputs such as data metrics and reports, virtual prompts, and real time charts of student attention as different examples of feedback.

Application: Entrainment, Therapeutic—Learning how not to be Creepy

Learning how to behave in a romantic or social context is difficult. While many online sources promise to teach "pickup artistry," these systems are often geared toward gullible people and against the "targets" they want to prey upon. This system would allow the user to prototype romantic and other interactions in a shared VR environment that teaches people how to develop appropriate boundaries while also encouraging respect and humanity. This would also be useful to people with all types of social anxiety disorder, to help them learn how to interact with people in a healthy way.

For example, Morley has zero success with the women he wants to date. He has no idea what to do about it. When he asks his friends sincerely, they all agree that he has trouble understanding how to draw appropriate boundaries—what is respectful behaviour, which jokes are okay to make, and how close he should stand to people without invading their personal space. His therapist suggests he log regular sessions with the system according to some embodiments to prototype interactions with women, and develop appropriate boundaries. Morley enters a virtual environment where he can practise speaking to women. His therapist also enters the environment with him, to see how he's doing. During his conversations with women in the virtual environment (VR events), Morley receives visual cues (as feedback) like colour changes, changes in music, or icons and alerts that tell him how his overtures are being received by the people he's talking to. These are based on accumulated aggregate profiles from other players, and from baseline brain state data gleaned from other users who have elected to make their anonymized data available to developers. A simple red/yellow/green card system may be used in some examples for Morley to learn more about how his behaviour is impacting the people around him, and whether or not they want him to continue behaving in that manner. When he notices yellow or red cards, he can ask for further assistance and find out what he's doing wrong. In the virtual environment, other people feel safer telling him what he's doing well and what he's doing badly. They can be more honest. Based on existing user data gleaned from other wearers, he learns how to communicate with women more respectfully. Eventually, Morley develops better communication skills that help him in real life.

Embodiments described herein can translate inputs like EEG data, eye-tracking, pulse, temperature, and motion into outputs like data reports, dynamic chances to the virtual environment, visual cues, colourful auras, text messages, and chimes to alert the user to their behaviour as feedback.

Application: Virtual Telepresence Presentations Enhanced by EEG VR to Show Real-Time Shifts in Audience Emotions Most leadership training experiences don't offer real time brain-state data. This system does allow for exactly that. Speakers, Executives and others within leadership positions can gain real time understanding of audience reactions to their speeches and presentations as feedback. This way, they can gauge the effectiveness of a given speech or presentation, and adjust on the fly, especially if they have made a mistake or said the wrong thing.

For example, Joan is a major executive who is delivering a presentation at the yearly developers' conference. She wants to know what effect she's having on the audience in real time. Some, all, or a percentage of the audience are also wearing wearable computing devices of the present invention. Some of them are in the room with her, and the others are in other locations, either watching via the internet or in other places in the conference centre. She uses a wearable computing device of the present invention to gauge audience reactions as she speaks. Seeing the reactions of a whole virtual audience through the VR goggles provides a very strong, realistic and instant form of feedback to the speech giver that is tied very closely in time to the wording or intonation that may have caused a pleasant, or adverse reaction from the audience. When Joan makes a joke, she sees the emotional shift in the audience as they pay closer attention. As Joan leads the audience through her speech, she's able to see how they react to what she says via the wearable computing device. She witnesses audience reactions through her device, which manifest as colour changes or icons or popups or logos in her vision. As she learns more about the audience's reaction, she can edit out certain jokes, or speed up the presentation to keep audience attention. Using this information, Joan delivers a far more effective presentation. System inputs may include EEG, EMG, ECG, GSR linked to VR events. System outputs may include visual/vibrational feedback cues.

Application: Entrainment, Therapeutic, Entertainment—Arousal Level Modulating Virtual Sexual Encounter There are many methods of couples therapy available to the people who are interested in them. Very few offer enhanced sexual awareness based on real time changes in brain-state, or the enhanced sexual focus and greater intimacy between partners when that data is made available. The strength of this system is that it makes plain all the things that can be difficult to express during an intimate encounter, even if that encounter is with a trusted individual. With brain-state data, suddenly feelings of discomfort or pleasure are easy to recognize, and consent is far simpler to discern.

For example, Paul and Linda are in a sexual relationship. Both of them have problems focusing on sex. One has ADD, and the other has stress at work that makes it difficult to "turn off" thoughts about the job. This means that both of them have a tough time being truly emotionally and physically intimate with each other, when they do have sex. Their sex therapist prescribes sessions with the wearable computing device according to some embodiments described herein that will help them focus on each other during sexual encounters, as a means of tuning out unhelpful thoughts and bringing their attention back to each other. Either together or separately, both partners can wear a wearable computing device that gently focuses their minds while also subtly arousing them. This could be purely visual stimuli like traditional pornography, or hearing the sounds of sexual activity, or even listening to a florid audiobook. As arousal increases (desired brain state), the system helps detect both levels of arousal and levels of focused attention. As the sensors pick up greater focus, more arousing material comes through the device as feedback—images, sounds, etc. all arrive in a steady stream. When Paul or Linda is unfocused, the stream fades out. Eventually, Paul and Linda learn how to "tune out" unwanted stimuli and focus only on what is arousing them. They incorporate the system routine into the "cognitive foreplay" phase of their sexual encounters, as a lead-up to physical foreplay and sexual activity.

System inputs may include EEG, EMG, ECG, Accelerometer, GSR. System outputs may include auditory, visual, vibrational.

Application: Entertainment, Diagnostic/Monitoring—Virtual Movie Storyline that Modulates Based on Emotions Many narrative platforms, from novels to comics to films, have offered alternate endings or differing branches of events. Very few can tailor that experience in a real time dynamic way, such as the system of the present invention can do. Further, this system offers an enhanced movie experience; an opportunity to "choose your own adventure," based on real time emotional reactions.

For example, David is watching a movie at home via his wearable computing device 105 of the present invention. The device continuously takes readings from him about whether his attention is drifting or remaining focused. During times when the system reads a lack of focus, it sends a signal to the wearable computing device 105 to make the content more exciting: there's an abrupt change in the music, or the colours become more saturated, or the contrasts sharpen. Over time, the wearable computing device shows David several different versions of the same film, based on his responses. David can save these different versions of the film and share certain moments from them with his friends via a social network.

Application: Entertainment, Diagnostic/Monitoring—Virtual Report that Modulates Based on Emotions For example, Roscoe has to read multiple productivity reports, as part of his job. The reports are very boring, though, and Roscoe has a hard time focusing on them. He inputs some of the reports into a wearable computing device 105 of the present invention, which allows him to read the reports without distraction. Not only are the reports right in front of him when he sits down to read them, the device helps detect his focus and distraction. When Roscoe experiences distraction, the device senses the change in baseline brain state and provides him with stimuli to keep him on task as feedback. This stimuli could be a simple chime or sound, or perhaps a colour change, or maybe just a quick reminder text. The device records how long it takes Roscoe to read his way through a document and gives him progress bars to help him understand how he's reading and at what speed. The device also charts when he feels distraction based on the text or when he notices an error in the text, or when he registers surprise. It marks the text accordingly. These points in the text can become places for Roscoe to speak with the writers of the reports about their work.

Application: Therapeutic—Out of Body User Therapy

Physical therapy is a chore. And for patients with difficulty accessing clinics, actually attending sessions can be quite prohibitive. But with a wearable computing device 105 of the present invention, patients with physically debilitating injuries and illnesses can perform physical therapy in a fun environment, while their emotional responses and sensations of pain are monitored. This can remove some of the emotional burden from physio and occupational therapists, some of whom have difficulty judging when a patient should continue within a given activity. With data provided by the device, patients can train for longer, and therapists can see how they are actually performing without confirmation or other biases getting in the way.

For example, Liza has experienced a catastrophic automobile accident, and needs intense physical therapy to repair damage to her shoulder. However, she has a hard time focusing on her exercises, and finds them both boring and embarrassing, because she has such a hard time with them. Her physiotherapist advises that she perform her exercises in a virtual environment where she can focus on accomplishing the tasks. The physiotherapist also advises her to use EEG sensors to monitor her emotional responses to the exercises and her sensations of pain. Liza wears the device and performs a variety of activities in the virtual environment that stretch and use her injured shoulder. For example, she may play tennis or learn how to hunt with a bow and arrow. As she performs these activities, she not only uses the injured shoulder and helps to heal it, but the device detects her sense of having made errors (ERNs), and her ability to focus on the exercises. Over time, Liza learns how to focus appropriately on her exercises. She also feels less stress and anxiety while using her injured shoulder.

System inputs may include EEG; gyroscope; accelerometer; moisture detection; temperature. System outputs may include dynamic changes to virtual environment based on brain state; data stream; progress reports as feedback.

Application: Data Gathering—how do Different Architectures or Interior Designs Make Me Feel?

Many design companies rely on extensive prototyping to help decide what the best design for a given object is. But with the wearable computing device 105, in some example embodiments, they can gather real time brain state data about how objects and affordances are being used by the intended audience, or research group. This system provides a valuable contribution to user productivity based on response to ergonomics, affordances, and designs based on disability.

For example, there may be an application for developing a new interior design philosophy for a new office building. Before going through the costly process of constructing the actual interior, the system can engage in user testing of a variety of environments. Office workers may wear VR headsets with EEG-reading technology built into the headset. The test subjects are exposed to a variety of ergonomic options for the new office space, i.e. open-concept vs. closed offices; various colour combinations; various seating options; lighting levels. Employees engage in simulated work tasks while their ergonomic environments are adjusted. The EEG-reading device in the VR headset captures their moods and thought processes during each iteration of change that an application wishes to test. The brainwave responses of the test subjects are recorded in relation to whether each change produces a positive or negative result in terms of metrics that benefit productivity. After the testing period, the system can suggest an ergonomic scheme that maximizes a productivity response.

System inputs may include EEG; gyroscope; accelerometer. System outputs may include data.

Figure 12:
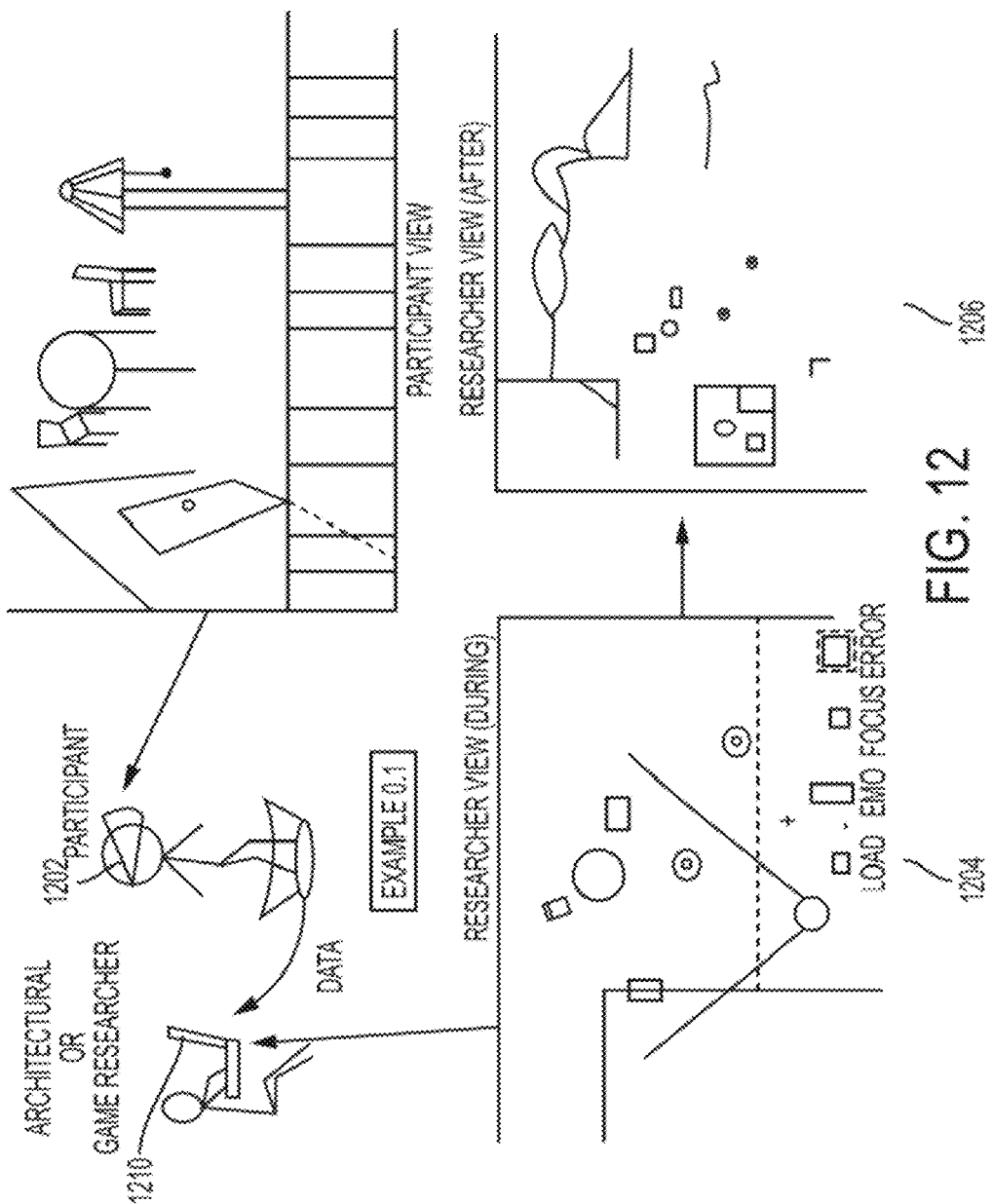
FIG. 12 shows an example user interface for architectural design or game design to generate or update aspects of the VR environment according to some embodiments.

An example of this application may be seen in FIG. 12 which shows a user interface for architectural design or game design. This drawing shows the participants view of an architecture. The researcher view provides the user's field of view in real time during the user assessment. The researcher view after shows a colour coded heat map of the various biological states the user was in when in a certain part of the architecture which may be an example of feedback. This may allow the researcher to redesign the architecture based on map of environment of user's brain states. The system can aggregate multiple participants in this way to generate analysis map.

Figure 13:
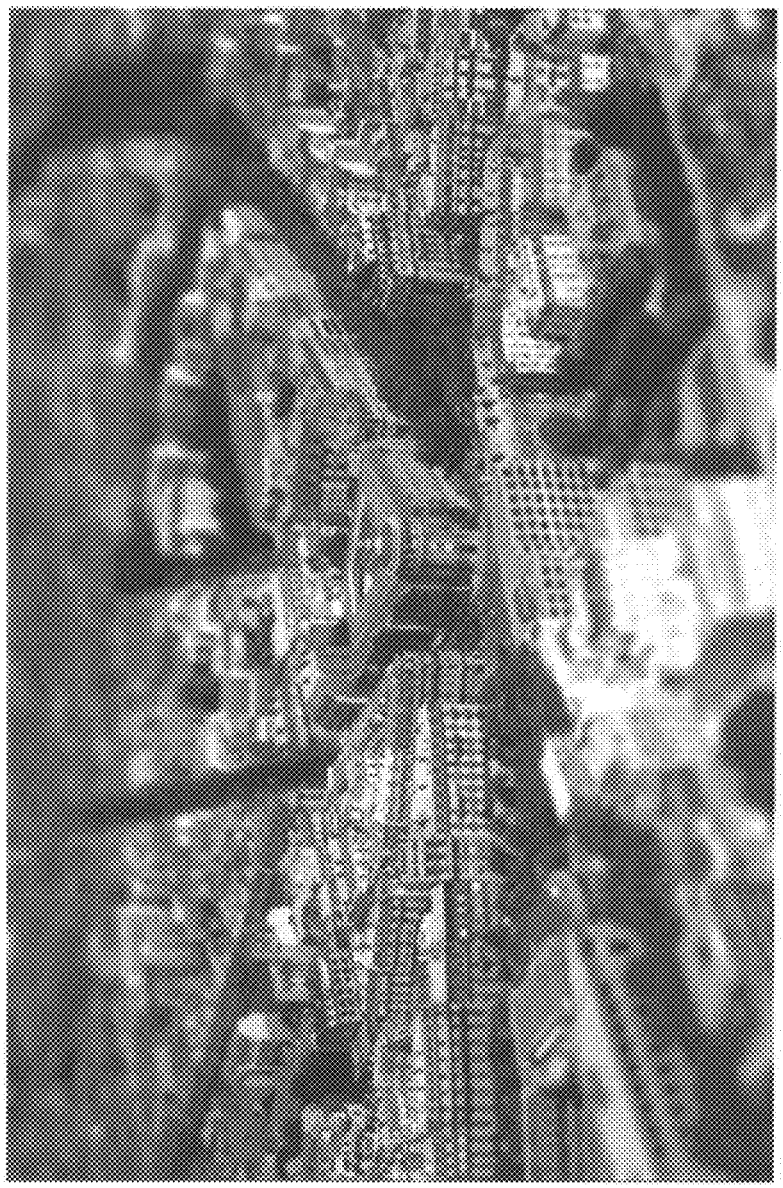
FIG. 13 shows example content of a VR environment of a user who is working and who desires to focus on what he is doing as an aspect of training according to some embodiments.
Figure 14:
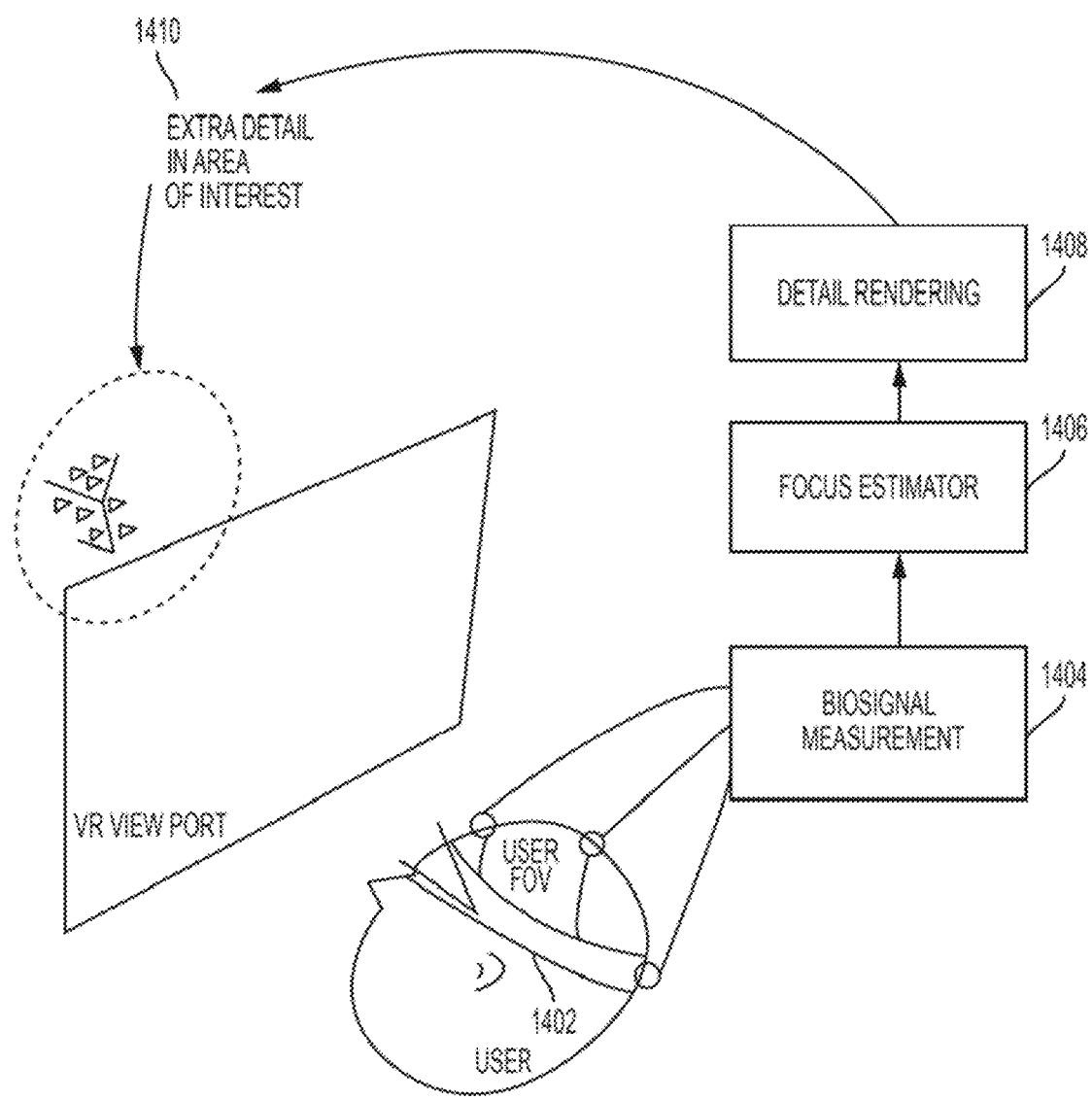
FIG. 14 shows a schematic of an example magnification and extra details of a user focusing on an area of interest according to some embodiments.

Another example may be seen in FIG. 13 showing a visual representation 1300 of the VR environment of a user who is working and who desires to focus on what he is doing. A bio-signal enabled headset can be used such that the rendering engine diminishes their field of view when they are not focusing to limit sensory input when they are trying to re-cultivate their attention. The system may limit the FOV by darkening edges, or to change the information density (polygon level changed). Saturation may be modified. Detail may be made to disappear. The rendering may be done so that changes in user state are not too intense so that user doesn't get information shock. A Converse operation can also useful for achieving the same goal: as the user focuses, the amount of surrounding information decreased so that the central information of interest is intensified. This allows more information to be incorporated when the user wants it. If the user focuses on something then more detail will appear. VR effect can also include zooming. Ken burns like effect for VR. When the user is focusing, the region of interest becomes magnified as feedback or effect (in a 3D word this can be done with greater effect than 2D tricks of focus) and with extra details as shown in FIG. 14. A user may have a wearable device 1402 with bio-signal sensors to provide bio-signal data to for bio-signal measurements 1404, focus estimator 1406, and detail rendering 1408 operations (implemented by wearable device 1402 or another device). The bio-signal measurements 1404, focus estimator 1406, and detail rendering 1408 operations may determine a user state score to provide feedback as a visual representation 1410 of extra detail in an area of interest. A desired user state may be based on a level or threshold of focus as determined based on the received bio-signal data from wearable device 1402.

Application: Therapeutic, Entertainment—Transport Entertainment System

In-flight entertainment is usually screen- or paper-based. This system provides stimulating entertainment and distraction to people with intense phobias during times of extreme stress, such as during a turbulent flight. There's a double-level of stimulation that helps passengers calm down using the system of the present invention, while also distracting them with VR technology. Both of these elements work in conjunction to help passengers feel safer during their flight. For example, Billy is afraid of flying, but he has to do it regularly for work. In order to get over his fear of flying (or at least make the flights more endurable), his therapist suggests to him that he purchase a wearable computing device according to some embodiments to distract him during flights. During his next flight, the aircraft is experiencing turbulence. The device detects Billy's stress through EEG, and detects how bad the turbulence is through an accelerometer and gyroscope that judges how much he is moving around. The VR system counteracts the turbulence by immersing him in a different world. He wears a VR headset with EEG sensors baked into the hardware that throws stimuli at the virtual environment until Billy is suitably distracted and calm. Billy's virtual environment is constantly changing to reflect the time of day, etc. His EEG sensors detect his level of alertness/drowsiness. If Billy indicates to the system that he wished to stay awake, the virtual environment will assist him by providing an alert if he is getting drowsy. Similarly, if Billy indicates to the system that he wishes to fall asleep, the VR environment will change to be conducive to rest. Billy can program the system in "sleep mode" to awaken him at a certain time. Important announcements from the captain/train driver, etc. can be fed directly into the VR system and given priority so Billy can respond to them immediately. If Billy suffers from a fear of flying, the VR system will compensate by activating a meditation program or by filtering out distressing noises/visual stimuli.

Application: Therapeutic, Entertainment—Using Biometric Inputs to Modify Anxiety/Stress Levels Based on Desired User Environment This system adds a stress test component to in-game activities that are another way of playing the game or judging progress. For example, Dan is an avid gamer. He likes high-action shooters like Call of Duty or Halo. Dan plays in a virtual reality milieu using a VR headset that contains EEG-reading sensors. Dan wants to increase his performance in these games so that he can perform well under high levels of stress. The VR game presents a series of tests that put Dan under simulated stress events—i.e. a sniper attack, etc. The EEG sensors in Dan's VR headset asses—his emotional/stress state during these tests and provide him with updates based on his performance. Dan's performance during these "stress tests" can unlock different achievements and new missions. If Dan has a stressful job—i.e. in the military—these "stress tests" can provide a valuable metric for gauging how he will perform in real-life situations that are stressful.

Application: Entrainment—Deliver Educational Content Effectively to Students (Making Learning Fun)

This system gives students another way of learning information in a distraction-free environment where they can focus on their studies and receive feedback from their brain state. For example, Sally is a student. She learns in a classroom that uses VR equipment. She wears a VR-enabled headset during classes. Lessons are delivered with VR technology: i.e., she is in the middle of a virtual solar system oriented around her. EEG sensors in the headset monitor Sally's levels of attention and engagement with the subject matter are determined and scored against desired states. When Sally loses her focus, the system alerts her teacher as feedback; it also provides her with extra stimuli as additional feedback so that she can re-focus more naturally. The rate at which content can be delivered to Sally is modified automatically by the VR headset she wears. Eventually, Sally's in-class and academic performance improves, as she learns to focus on the tasks at hand.

Application: Therapeutic—Couple Counselling Using VR Technologies to Enhance Therapeutic Outcomes Many systems of couples therapy focus solely on cognitive behaviour therapy, or "talk therapy," wherein each partner takes turns trying to make themselves clear. This system allows couples and other partners to mindfully focus on their relationship with real time data streams from each partner, so they eventually learn how to "put their heads together" to solve problems and co-exist more peacefully. For example, Ted and Carol are a married couple who are receiving relationship counselling using virtual reality-enabled technologies. As their counselling sessions progress, EEG-detecting sensors in their VR goggles monitor their brain states. During the course of therapy, the therapist can instruct Bill and Carol to focus on their mindfulness; the EEG-sensing technology can detect when their mindfulness state is suboptimal through scoring. The therapist can direct Bill and Carol to focus on their breathing or other techniques to enhance mindfulness and relaxation. Bill and Carol can participate in shared trust exercises that are mediated through their common virtual environment. For example, they can perform trust falls, or defeat a common enemy together in a virtual reality game. This process encourages shared empathy between the couple. If one partner is disturbed, the other sees this as a direct visual manifestation, such as an aura or an icon that appears within the virtual environment and says what the other person has difficulty saying.

The system can translate EEG input along with motion-sensing, eye-tracking, temperature and pulse into dynamic visual feedback information in an immersive virtual environment, almost like an "alarm bell" for when a conversation has gone bad or broken down between two people.

Application: Therapeutic, Entrainment—Sensitivity Training in a VR Environment

This system allows corporate executives and others in leadership positions to see themselves in the third person (as an example of feedback) as they are behaving with their employees.

Jorge works for a large, multinational corporation. As part of disciplinary training, Jorge is compelled to undergo a sensitivity training seminar that uses VR technology. The idea is to expose Jorge to a variety of situations in which he does not enjoy the privilege of his dominant position in the social hierarchy. When the seminar begins, Jorge is invited to put on a pair of VR-enabled goggles that contain EEG-sensing equipment. The other members of the sensitivity training group are also instructed to do the same. The training program begins: Jorge sees himself—i.e., his avatar in the constructed VR environment—from an external position, so it is like Jorge is witnessing himself and his actions in the third person. As the sensitivity training seminar proceeds, Jorge views himself under changing situations, i.e.: he sees himself as part of a different racial/ethnic group; as part of a group with a different ability, status, etc. The other people in the group observe Jorge's avatar in his new states as they cycle through, as per the instructor's wishes. Both the EEG signatures of the group and of Jorge are recorded during the testing period. Jorge can watch as the EEG patterns of the other people in the therapy group are "played back" during the course of the therapy session; they are played back and interpreted visually much in the same way as a song is played back and visually interpreted as part of a "visualization program" for music tracks. In this way, Joe can see how his transformations from physical state to physical state are "interpreted" by others in his group as actual EEG brainwave data. Joe reports how this experience has changed/benefitted him as part of a post-group post-mortem. The instructor can therefore gauge the effectiveness of the class based on how Jorge interprets the EEG patterns of the other participants.

Application: Therapeutic—Meditation Simulation for Environments Not Conducive to Restful Contemplation While meditation can be felt, it's hard to quantify in a way that other people can understand. It's also easy for people doing meditation to feel as though they've slipped behind or aren't making enough progress. This creates a distraction that is anathema to the act of meditation itself. Embodiments described herein may allow people who are meditating to see their progress as feedback. This can be helpful for people who have been asked to meditate as part of cognitive behavioural therapy, or to bring down blood pressure, or manage chronic pain. For example, Chenelle wants to participate in a meditation program at home, but her home is crowded/noisy/not conducive to mindfulness. To overcome this environmental obstacle, Chenelle dons a pair of VR goggles. The goggles provide a virtual meditation environment in which the area surrounding Chenelle is free of distractions. This VR environment can be mapped using a device which contains sensors for mapping a 3D environment, such as the Google Tango phone. Chenelle can participate in either a walking or a sitting meditation practice with the distracting elements of the environment she's in blocked out. As Chenelle practices her meditation, her EEG state is being monitored. Chenelle can visualize her EEG state during the meditation practice; it can be presented like a music visualizer—a series of peaks and troughs can become visible travelling towards her corresponding to her mental state. This can allow Chenelle to see how her meditation is progressing, i.e. whether she is meeting her meditation goals in terms of relaxation, etc. Chenelle can then optimize her meditation practice to meet specific goals by modifying her breathing or some other variables to create a different outcome during the meditation practice.

Embodiments described herein translates EEG data, heart rate and pulse detection, and eye-tracking to generate feedback outputs like real time dynamic changes to the virtual environment (such as a change in music or ambient sound, or shifts in light, transparency, or opacity, or topography), while also creating data for reports that wearers could opt into or share with friends and supporters.

Application: Therapeutic—Creating A Virtual Meditation Group Using VR Technologies In a globalized world, it's easier than it ever was before to find like-minded individuals and spend time with them online. But it's rare to find a digital-friendly meditation studio, or people to meditate with over long distances. This system aims to change that, by creating virtual meditation spaces where people from all walks of life can drop in for a re-focusing session. For example, Grant wants to participate in a group meditation session, but there are no meditation groups meeting near him. Grant puts on a pair of VR goggles which include EEG-sensing technology. The goggles are connected to a computer network that contains a virtual "meditation salon", much like a virtual chat room. Other participants who want to partake in the collective virtual meditation experience can "dial into" the salon. Each person who is engaging in the shared virtual experience is represented in the "meditation salon" by an avatar. The meditation group is guided by a leader who issues instructions that the rest of the group follows. As the group proceeds with their meditation session, their EEG data is collected. As the meditation session proceeds, each member of the group can decide whether to keep their eyes closed or open. If they decide to open their eyes, they are able to look at other member of the group. The EEG readings from other members of the group affects the appearance of their avatars. e.g. if the person is relaxed, their avatars can glow blue; if they are tense, their avatars would glow red. The individual participants can look at their own avatars to determine how they are proceeding with the meditation session; their own avatars will change colour like those in the rest of the group. Emotions can also be displayed on the avatars; i.e. the words "ANGRY" or "ANXIOUS" can appear on their faces. Guided meditations can be programmed so that instructions issued by the group leader are interpreted visually. i.e. the meditation leader says, "Imagine a beam of bright white light emanating from the top of your heat. This light pulses in time with the rhythm of your breath. This visual metaphor can be translated literally onto the avatars in the meditation group; users can see beams of light emanating from the tops of the heads of the other participants in the group.

Embodiments described herein can translate EEG data along with motion detection, eye-tracking, and other physical and brain-state data into dynamic real time experiences in a virtual environment, such as text alerts, shifts in colour, changes in music, and changes in player relations as examples of feedback.

Application: Therapeutic, Entertainment—Caring for a Virtual Pet in a VR Environment FIG. 11, the system provides a therapeutic environment for people that is also entertaining. For example, Danielle owns a virtual pet that she takes care of in a virtual environment. She puts on her VR goggles to visualize the pet in a specially-constructed 3D environment. The pet responds not only to Danielle's actions (i.e. feeding it; entertaining it, nurturing it) but also responds to her emotional state as different forms of feedback. While Danielle cares for her virtual pet, she wears an EEG-detecting device. The device measures her brainwaves and changes the characteristics of the virtual pet accordingly to provide visual feedback. For example, the pet changes colour from green to red when Danielle is upset; it changes back from red to green when she enters a relaxed state. Alternatively, the pet can change its own behaviour: irritated, relaxed, angry, etc. The pet can be used as a mindfulness/meditation aide—Danielle tries to get her pet to change colour to a certain state to match whatever mindfulness goals she is aiming towards. Danielle can also enter a virtual "pet club" to interact with other virtual pets and their owners. These owners/pets appear in a networked, constructed virtual world. Danielle can interact with other pets and their owners and can change the emotional/physical states of the pets. If other pet owners in the virtual space are wearing EEG-sensing devices, their mind state is visible to Danielle as various manifestations on their avatars—changing colour to red when distressed; to green when relaxed, etc.

Application: Data Gathering—Using Immersive VR Environments to Test Advertising Effectiveness Most market research depends on answering survey questions or performing a quiz. Embodiments described herein may provide real time brain state data to market researchers and other data gatherers about how subjects feel about specific stimuli. This data is a complement of physiological data to existing qualitative data in research settings, whether they are market-driven, sociological, or purely scientific. For example, Jon is in charge of running a focus group to determine the effectiveness of a TV ad. Jon engages with a focus group audience who are equipped with VR goggles. These goggles contain EEG-reading hardware. In a purpose-built VR environment, Jon instructs the focus group subjects to watch an ad for testing. As the participants watch the ad, Jon is able to visualize their emotional responses in real time as a stream of data from the EEG readers on the participants. For example, as Jon watches Barb—who is part of the focus group audience—she can see that she is being irritated by the ad because her avatar in the VR environment has turned red. Similarly, Jon can see that Kevin—another focus group participant—is enjoying the ad because the colour of his avatar has shifted to a green hue. Jon can show multiple versions of the same commercial to the focus group and have the ability to detect their real time reactions instantaneously.

Embodiments described herein may take data from EEG sensors and translates it into feedback outputs like data metrics reports on attentional bandwidth among users. It can also help marketers and others determine how to tweak media in real time based on real time brain-state changes.

Application: Therapeutic, Entertainment, Design—Using Immersive VR Environments to Facilitate Engineering Testing High-pressure systems like nuclear reactors, hydro-electric dams, and other pieces of infrastructure can seem quite daunting to the people who are training in how to maintain them. Embodiments described herein may provide a dynamic, responsive virtual environment that helps train professionals and offers them feedback on their stress levels during training exercises. Using this data, professionals can examine their weak spots and learn exactly where they should be focusing while performing these high-pressure tasks.

For example, Bill works for a hydroelectric utility. He is tasked with retrofitting one of the turbines at the hydro plant he works at. He and the design team enter a VR environment corresponding to the environment inside that turbine. Some of the members of this team are across the country from Bill and his co-workers, so meeting in a virtual environment makes the most sense. He and the team can try various engineering solutions to solve the problem at hand, or investigate different design solutions from available contractors and vendors. As they sketch out different solutions, these solutions appear inside the virtual world. Every so often EEG-reading devices in the VR headsets can take the emotional "temperature" of the participants to see how well they are performing together.

Embodiments described herein can translate inputs like EEG data, motion-detection, eye-tracking, and other data into a dynamic virtual environment that reflects changes in infrastructure design or device design. It can also indicate how different users react to specific designs, such as a flash of recognition, disgust, or the sense a given design being a mistake.

Application: Entrainment, Medical—Using Immersive VR and EEG to Practice High-Tension Operations Many training exercises can prove too dry, meaning that the people taking them aren't truly prepared. Embodiments described herein may provide a dynamic, responsive virtual environment that helps train professionals and offers them feedback on their stress levels during training exercises. For example, Kim is a surgeon. Kim is going to perform a very difficult operation, and needs to practise before actually getting into the theatre with his patient. Kim wears a wearable computing device of the present invention while watching a simulation of the surgery in question. Kim downloads a simulation of the surgery and uses the system to develop skills at performing difficult parts of the surgery. He learns the rhythm of the surgery, as well as how to handle surprises like losses in blood pressure or sudden changes in heart rate. The system generates a report for Kim at the end of each session to help him see when he felt most anxious, and which parts of the surgery he might feel most anxious about. The report also tells him when his mind wanders or when he's distracted during the surgery simulation. When Kim actually performs the surgery in real life, he feels a great deal more confident and calmer. The surgery is successful.

Application: Entrainment, Military—Using Immersive VR+EEG to Practice Activities The system may provide a dynamic, responsive virtual environment that helps train professionals and offers them feedback on their stress levels during training exercises. For example, Joan works as part of a bomb disposal unit. Before she ships out, she has to log several hours of practise defusing bombs and other explosive devices in a variety of environments. Joan wears a wearable computing device of the present invention to practise working with multiple types of explosives. She downloads a suite of environments and challenges that represent what she will experience overseas as part of her unit. The environments are rendered in her VR unit, while the system reads her brain state as she performs the task. As the system reads her brain state, it notes when she feels anxious or perceives herself to have made a mistake (ERN). The system generates a report after each session that shows her what she feels most anxious about, and when she was distracted. Over time, Joan grows more confident.

Application: Data-Gathering, Entertainment—Using Immersive VR as a "Pay-Per-View" Client for Live Events, in Exchange for Brainwave Data For people who want to attend events "live" and contribute to them (such as sports broadcasts or political conventions), there is a value in their brain state data. This system can harness that data and feed it back to others who are in attendance.

For example, Tom is a member of the federal Liberal party. He wants to attend the party's annual convention but is unable to go in person. There is a roving 3-D camera at the event that captures key moments in the event. Tom is able to "dial into" the camera to access the feed—thus giving him the experience of actually being in the space. This is not technically a computer-generated "virtual" environment, but the AV content streaming from the convention constitutes a digital data stream just as much as virtual content coming from a computer. There is an EEG-reading device "baked into" the VR headset that Tom is using. The EEG device will collect valuable metrics about the convention—i.e. Tom's reaction to various speeches; his feelings of positivity or negativity towards candidates, etc. This data can be used by party leaders, polling firms, etc. Tom enters into an agreement with the party that the metrics collected from his EEG be used for whatever purposes they desire in exchange for his ability to access the data stream. This technology can be extended to other types of live events, e.g. pay-per-view sports or concerts. In each case, the client would exchange the data collected from his EEG device—plus the application of a possible fee—for the data stream from the event. The live TV stream from the event could be merged with other data; for example, if the viewer is watching a UFC fight, stats on competitors could be summoned at will and be merged into the general viewing milieu.

Embodiments described herein may allow users wearing their wearable computing device to gather brain-state and reaction data on themselves based on EEG monitors, eye-tracking, motion, temperature, and other responses and share it with a crowd of people also in attendance at the same event. This allows researchers to create a portrait of the "mood" of an event, while also allowing audiences to engage together at a more intimate level.

Figure 16:
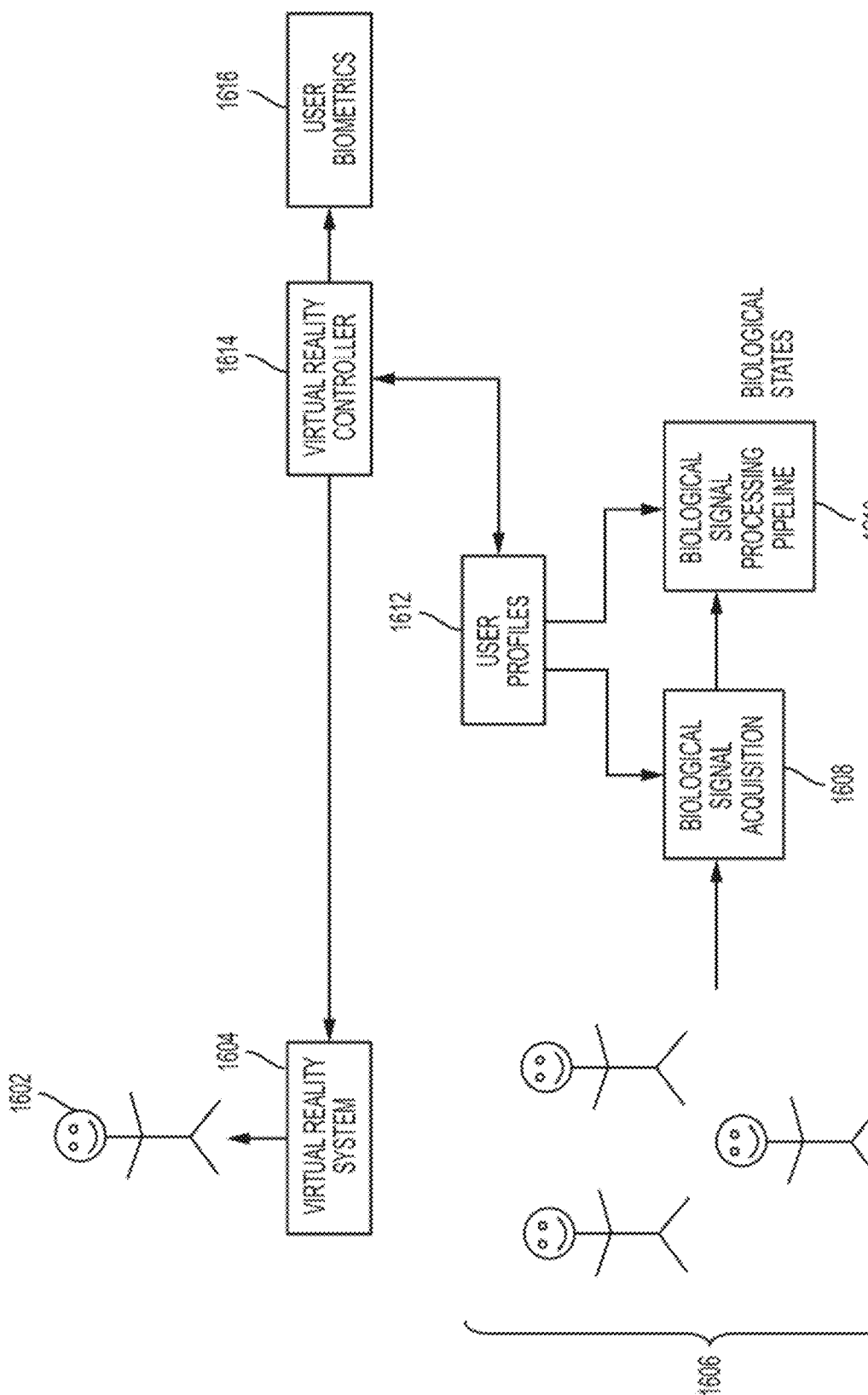
FIG. 16 illustrates a schematic view of an implementation of another example system according to some embodiments.

FIG. 16 shows an instance where one user's 1602 VR environment (as provided by a VR system or wearable device 1604) may be modified based on biological signal acquisition of one or more other users 1606. For example, the user 1602 may be able to see the reaction of other audience members 1606 to the user's performance through the VR environment rendered by the wearable computing device worn by the user 1602. The other users 1606 may also have a wearable device with bio-signal sensors to provide bio-signal data to a bio-signal acquisition unit 1608 and a bio-signal processing pipeline 1610 to determine one or more user states. The bio-signal acquisition unit 1608 and a bio-signal processing pipeline 1610 may access user profiles 1612 stored in a data storage device to determine the user states. The user states may be scored to provide feedback to the user 1602 as visual representations in the VR environment. The other users 1606 may also access the VR environment using wearable devices and may have the same or different view from the other user 1606 to determine their user states based on VR events relating to all users 1602, 1606 or VR events generated by user 1602 that are observed by users 1606 to trigger a brain state reaction as described herein. A VR controller 1614 may trigger updates in the VR environment as feedback and may also trigger VR events to evaluate brain states of users 1602, 1606 in relation to those VR events. The VR controller 1614 may authenticate user or receive additional bio-signal data from user biometric devices 1616.

Figure 15:
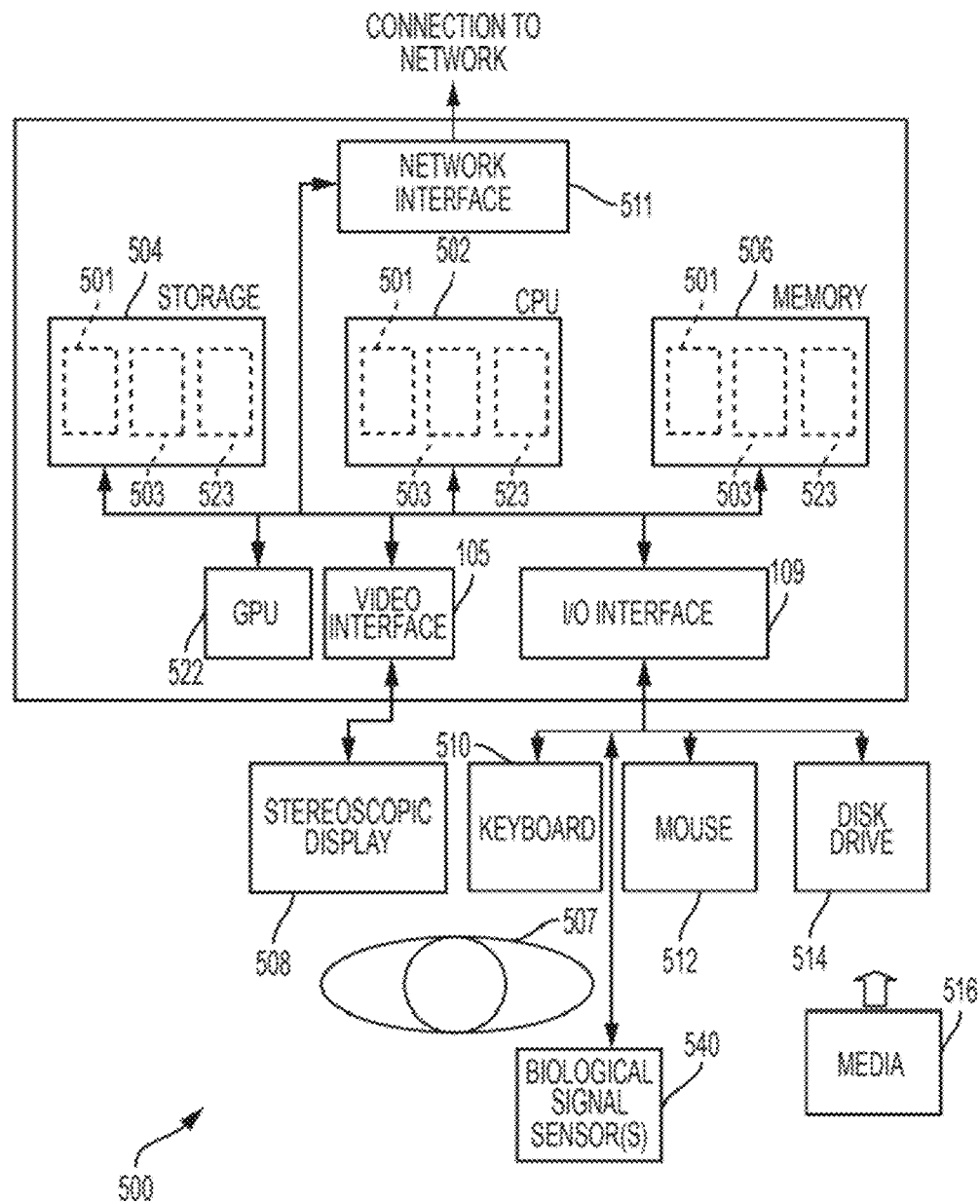
FIG. 15 illustrates a schematic view of an implementation of a computer device.

The present system and method may be practiced in various embodiments. A suitably configured computer device, and associated communications networks, devices, software and firmware may provide a platform for enabling one or more embodiments as described above, such as for example the computing device 150 and the other computing device 160. By way of example, FIG. 15 shows a schematic view of an implementation of a computer device 500 that may include a central processing unit ("CPU") 502 connected to a storage unit 504 and to a random access memory 506. The CPU 502 may process an operating system 501, application program 503, and data 523. The operating system 501, application program 503, and data 523 may be stored in storage unit 504 and loaded into memory 506, as may be required. Computer device 500 may further include a graphics processing unit (GPU) 522 which is operatively connected to CPU 502 and to memory 506 to offload intensive image processing calculations from CPU 502 and run these calculations in parallel with CPU 502. An operator 507 may interact with the computer device 500 using a stereoscopic video display 508 (or 2D display) connected by a video interface 505, and various input/output devices such as a keyboard 510, mouse 512, and disk drive or solid state drive 514 connected by an I/O interface 509. Other types of input/output devices may also be interfaced with the computer device 500, such as game controllers, including various types of gamepads, gesture controllers, and motion detectors or analyzers. The display 508 may be integrated into the computer device 500. Biological signal sensors 540 may also be connected to the computer device 500 through I/O interface 509 and may be activated/deactivated or otherwise triggered through the I/O interface 509. Each biological signal sensor 540 may operate independently or may be linked with other biological signal sensor(s) 540, or linked to other computing devices. Each biological signal sensor 540 may transmit data to the CPU 502 through the I/O interface 509. In known manner, the mouse 512 may be configured to control movement of a cursor in the video display 508, and to operate various graphical user interface (GUI) controls appearing in the video display 508 with a mouse button. The disk drive or solid state drive 514 may be configured to accept computer readable media 516. The computer device 500 may form part of a network via a network interface 511, allowing the computer device 500 to communicate with other suitably configured data processing systems (not shown). The application program 503 may include instructions to implement aspects processes described herein, including training processes that may involve receiving and processing manual input or bio-signal data or a combination thereof. Further, the application program 503 may include instructions to provide training feedback to the user based on a combination of user state score and a performance score, or other training feedback in various example embodiments.

It will be appreciated that any module or component exemplified herein that executes instructions may include or otherwise have access to computer readable media such as storage media, computer storage media, or data storage devices (removable and/or non-removable) such as, for example, magnetic disks, optical disks, tape, and other forms of computer readable media. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD), blue-ray disks, or other optical storage, magnetic cassettes, magnetic tape, magnetic disk storage or other magnetic storage devices, or any other medium which can be used to store the desired information and which can be accessed by an application, module, or both. Any such computer storage media may be part of the mobile device, tracking module, object tracking application, etc., or accessible or connectable thereto. Any application or module herein described may be implemented using computer readable/executable instructions that may be stored or otherwise held by such computer readable media.

Thus, alterations, modifications and variations can be effected to the particular embodiments by those of skill in the art without departing from the scope of this disclosure, which is defined solely by the claims appended hereto.

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be will be understood by those skilled in the relevant arts, with respect to both processes and any systems, devices, etc., described herein, a wide range of variations is possible, and even advantageous, in various circumstances.

What is claimed is:

1. A training apparatus comprising:
an input device and a wearable computing device with a bio-signal sensor, a sensor for measuring movement and a display to provide an interactive continuous virtual reality ("VR") environment for a user, the VR environment containing virtual elements, the bio-signal sensor receives bio-signal data from the user, the bio-signal sensor comprising a brainwave sensor;
the computing device having or in communication with a processor configured to:
as part of the interactive continuous VR environment, present content on the display where the content includes the virtual elements and has a VR event occurring within the interactive continuous VR environment, the VR event having one or more changes on the virtual elements in the VR environment, the VR event having desired user states;
continuously receive user manual inputs from the input device for user interaction with the virtual elements in the interactive continuous VR environment including during the VR event;
continuously receive the bio-signal data of the user from the bio-signal sensor and the sensor for measuring movement, including during the VR event;
process the bio-signal data to determine user states of the user, including brain states and a user head and eye gaze direction, during the VR event;
determine a user state score by comparing the user states of the user to the desired user states during the course of the VR event; and
modify the interactive continuous VR environment based on the user state score
wherein the user manual inputs are continuously received independent of the user state score.

2. The apparatus of claim 1 wherein the user states are processed using a user profile stored in a data storage device accessible by the processor.

3. The apparatus of claim 2, wherein the processor is further configured to dynamically update the user profile using the bio-signal data.

4. The apparatus of claim 1 wherein the processor is further configured to provide feedback to the user wherein the feedback is based on the user state score.

5. The apparatus of claim 1 wherein the brain states comprises one or more of ability of operator to learn; prediction error; and emotional state leading to impaired thinking.

6. The apparatus of claim 1 where
the computing device is further configured to:
revise the content based on the user state score where the user is further trained on the revised content.

7. The apparatus of claim 1 further comprising
a second display for presenting the content and a visual representation of the user states and manual inputs of the user in real time.

8. The apparatus of claim 1 wherein the computing device having or in communication with the processor is further configured to:
provide real time or near real time feedback to the user during the presentation of the content.

9. The apparatus of claim 1, wherein the VR event is associated with event time data and a portion of bio-signal data is associated with bio-signal time data corresponding to the event time data, wherein the processor is configured to identify a portion of the bio-signal data based on the event time data and process the portion of the bio-signal data to determine the user states during the VR event, the bio-signal time data synchronized to the event time data.

10. The apparatus of claim 1, wherein the VR event is associated with event time data and the bio-signal data is associated with bio-signal time data, and wherein the processor is configured to identify a time interval based on an expected response time for the VR event and the event time data, identify a portion of the bio-signal data based on the time interval and the bio-signal time data, and process the portion of the bio-signal data to determine the user states during the VR event, the bio-signal time data synchronized to the event time data.

11. The apparatus of claim 1, wherein the desired user state includes a distribution of desired brain states and wherein the determining of the user state score includes determining the deviation of the brain state from the distribution of desired brain states.

12. A training method implemented using an input device and a wearable computing device having or in communication with a processor, a bio-signal sensor, a sensor for measuring movement and a display to provide an interactive continuous virtual reality ("VR") environment for a user, the VR environment containing a plurality of virtual elements, the bio-signal sensor receives bio-signal data from the user, the bio-signal sensor comprising a brainwave sensor; the training method comprising:
as part of the interactive continuous VR environment, presenting content on the display where the content has a VR event occurring within the interactive continuous VR environment, the VR event having one or more changes on at least a portion of the plurality of virtual elements in the VR environment, the VR event having desired user states;
continuously receiving user manual inputs from the input device for user interaction with the virtual elements in the interactive continuous VR environment including during the VR event;
continuously receiving the bio-signal data of the user from the bio-signal sensor and the sensor for measuring movement, including during the VR event;
processing the bio-signal data to determine user states of the user, including brain states and a user head and eye gaze direction, during the VR event;
determining a user state score by comparing the user states of the user to the desired user states during the course of the VR event; and
modify the interactive continuous VR environment based on the user state score,
wherein the user manual inputs are continuously received independent of the user state score.

13. The training method of claim 12 wherein the user states are processed using a user profile stored in a data storage device accessible by the processor.

14. The training method of claim 12 further comprising: providing feedback to the user wherein the feedback is based on the user state score.

15. The training method of claim 12, wherein the brain states comprises one or more of ability of operator to learn; prediction error; and emotional state leading to impaired thinking.

16. The training method of claim 12, further comprising revising the content based on the user state score where the user is further trained on the revised content.

17. The training method of claim 12, further comprising presenting the content and the user states and manual inputs of the user in real time on a second display.

18. The training method of claim 12, further comprising providing real time feedback to the user during the presentation of the content.

19. The apparatus of claim 1, wherein the desired user states include a desired user head and eye gaze direction.

20. The training method of claim 12, wherein the desired user states include a desired user head and eye gaze direction.

* * * * *